(12) United States Patent
Pezaris et al.

(10) Patent No.: US 6,249,691 B1
(45) Date of Patent: *Jun. 19, 2001

(54) CHRONIC CHAMBER MICRODRIVE

(75) Inventors: John S. Pezaris; Maneesh Sahani, both of Pasadena; Richard A. Andersen, La Canada - Flintridge, all of CA (US)

(73) Assignee: California Institute of Technology, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/263,973

(22) Filed: Mar. 5, 1999

(51) Int. Cl.$^7$ .................................................. A61B 5/0478
(52) U.S. Cl. ............................................... 600/378
(58) Field of Search ................................... 600/373, 378, 600/383, 544; 606/130

(56) References Cited

U.S. PATENT DOCUMENTS 3,841,310 * 10/1974 Goldstein .............................. 600/378
5,927,277 *  7/1999 Baudino et al. ...................... 600/378

OTHER PUBLICATIONS

Gray, et al., "Tetrodes markedly improve the reliability and yield of multiple single–unit isolation form multi–unit recordings in cat striate cortex", Journal of Neuroscience Methods 63 (1995) 45–54.

Nichols, "A screw microdrive for adjustable chronic unit recording in monkeys", Journal of Neuroscience Methods 81 (1998) 185–188.

Data Sheet, Crist Instrument Company, Inc., III–3.

Microdrives & Related Equipment, Price List, Crist Instrument Company, Inc., p. 13.

"Semi–chronic Recording System", Frederick Haer & Co.

"At Last: An Affordable, Independently Advanced, Multi–microelectrode Drive System!", Frederick Haer & Co.

* cited by examiner

*Primary Examiner*—William E. Kamm
(74) *Attorney, Agent, or Firm*—Fish & Richardson, P.C.

(57) ABSTRACT

A chronic chamber microdrive ("CCMD") for neural recording. In one implementation, a CCMD for neural recording from a target site of neural tissue exposed by an opening in a skull of a subject, includes: an outer cylinder, having a longitudinal axis, positioned within the opening and rotatable within the opening; an inner cylinder positioned within the outer cylinder, such that the longitudinal axis of the outer cylinder is within a circumference of the inner cylinder and the inner cylinder rotates within the rotatable outer cylinder; at least one fine leadscrew, positioned longitudinally in the inner cylinder; at least one electrode for neural recording, where at least one of said electrodes is coupled to a corresponding one of said fine leadscrews, where said electrodes are positioned horizontally by rotating the outer cylinder and separately rotating the inner cylinder, and where said electrodes are positioned vertically by rotating said fine leadscrews.

26 Claims, 25 Drawing Sheets

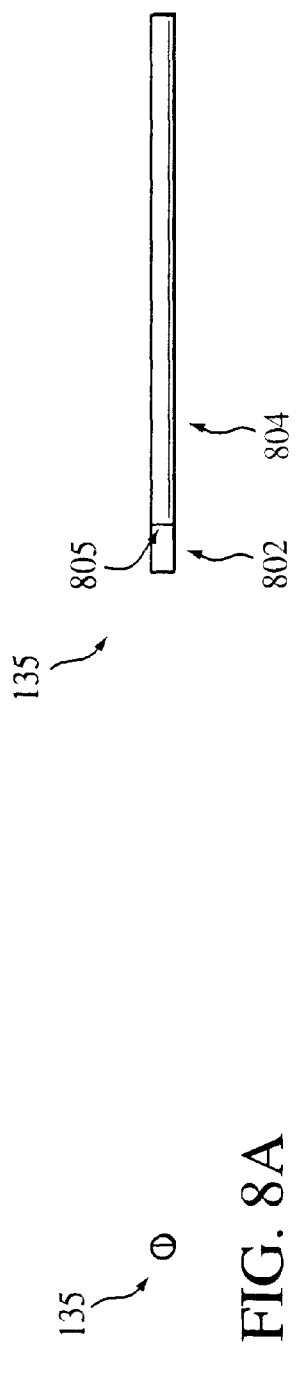

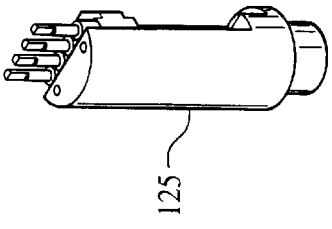
FIG. 17A  FIG. 17B  FIG. 17C  FIG. 17D
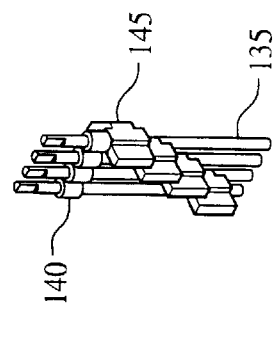
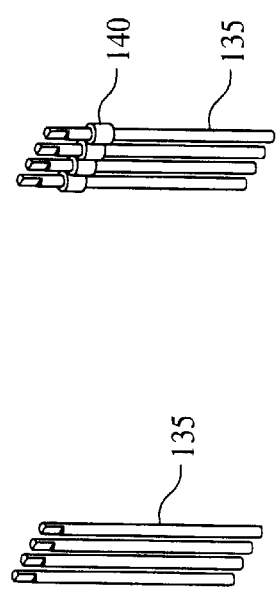
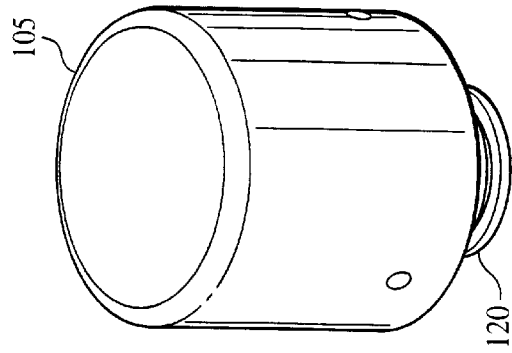
FIG. 17E  FIG. 17F  FIG. 17G  FIG. 17H
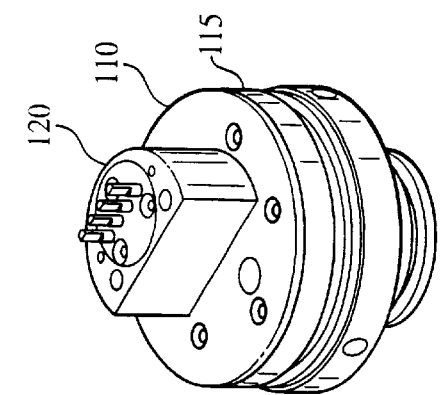
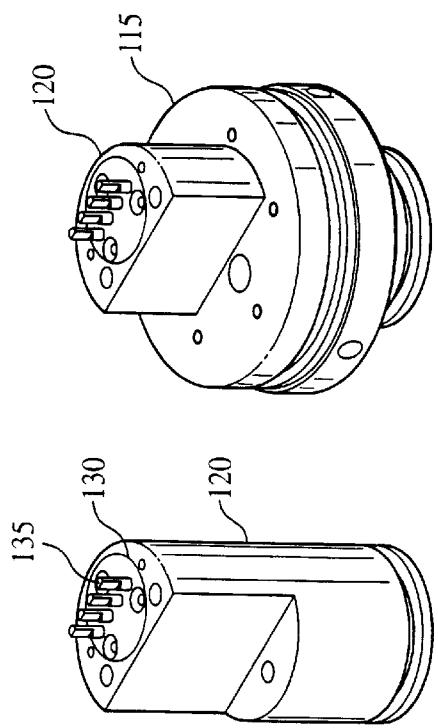

CHRONIC CHAMBER MICRODRIVE

The U.S. Government may have certain rights in this invention pursuant to Grant No. EY 05522 awarded by the National Institute of Health and Grant No. N00014-94-1-0412 awarded by the Navy, and Grant No. N0014-96-1-1257 awarded by the Navy.

TECHNICAL FIELD

The present disclosure relates to neural recording via electrode insertion, and more particularly to neural recording via electrode insertion using an implanted microdrive.

BACKGROUND

Neural recording typically selects different parts of the brain to obtain different information. One approach to neural recording includes extra-cellular electrode insertion. Extra-cellular electrode insertion typically involves the insertion of one or more electrodes into neural tissue. Conventional extra-cellular electrode insertion has traditionally followed one of two paths.

One conventional technique extra-cellular electrode insertion is a chronic technique, i.e. long term, such as more than one day. One or more electrodes are surgically implanted in the brain of a subject, such as an animal. In general, these electrodes are not subsequently repositionable without another surgical procedure. Any available motion is typically only in depth. Thus, the X and Y positions along the surface of the brain are fixed during surgery and the Z position into the brain is potentially adjustable. Using this configuration, experimenters can record from a small group of neurons for an extended time period. However, because this technique uses a surgical procedure to insert electrodes into the animal's brain, the experimenters typically can only record from the one collection of neurons corresponding to the surgical site in the animal. To accomplish additional recordings from different collections of neurons in the animal's brain, additional surgical procedures are required for each desired recording site. Due to the trauma of such surgical procedures, test animals typically cannot withstand more than a limited number of applications.

A second conventional technique for extra-cellular electrode insertion is an acute technique, i.e., short term, such as less than one day. This technique typically involves daily reinsertion of electrodes into an animals brain. A craniotomy is opened surgically, and is them covered by an implanted resealable cylinder. This cylinder is typically called a "recording chamber". The recording chamber includes a sealing plug. The sealing plug is used to maintain a closed seal so that intracranial tissue is not exposed while neural recording is not being performed. To perform neural recording, such as on a daily basis, the sealing plug from the recording chamber is removed and one or more electrodes are inserted in a target location in the neural tissue accessed by the craniotomy and defined by the recording chamber. An external device called a "microdrive" is typically used to position the electrodes. The microdrive mounts into the recording chamber and is adjustable in all three dimensions (X, Y, and Z). The microdrive is typically first set to an XY position and then scanned in the Z direction. When neural recording is complete, the microdrive and electrodes are removed from the recording chamber and the sealing plug is replaced, thereby sealing the recording chamber. In this acute technique, the experimenter typically has access to a larger total number of cells than in the chronic technique described above. However, the experimenter typically can record from a given group of cells for at most a single recording session, typically one day. This limitation arises from the exposure of intracranial tissue to an external environment caused by removing the sealing plug of the recording chamber. Prolonged external exposure of the target site tissue is potentially detrimental to the health of the tissue, impeding overall neural recording efficiency.

The inventors have determined that it would be desirable to provide the advantages of chronic neural recording as well as the positional advantages of acute neural recording using a microdrive.

SUMMARY

The present disclosure describes methods and apparatus implementing a chronic chamber microdrive ("CCMD"). In one implementation, a CCMD for neural recording from a target site of neural tissue exposed by an opening in a skull of a subject, includes: an outer cylinder, having a longitudinal axis, positioned within the opening and rotatable within the opening; an inner cylinder positioned within the outer cylinder, such that the longitudinal axis of the outer cylinder is within a circumference of the inner cylinder and the inner cylinder rotates within the rotatable outer cylinder; at least one fine leadscrew, positioned longitudinally in the inner cylinder; at least one electrode for neural recording, where at least one of said electrodes is coupled to a corresponding one of said fine leadscrews, where said electrodes are positioned horizontally by rotating the outer cylinder and separately rotating the inner cylinder, and where said electrodes are positioned vertically by rotating said fine leadscrews. In another implementation, at least one of the electrodes is replaced by a non-electrical probe.

Another implementation of neural recording with a CCMD includes: exposing a target site of neural tissue; positioning one or more electrodes at a first target position in the neural tissue using a microdrive device; recording neural activity at the first target position using said electrodes; repositioning said electrodes at a second target position in the neural tissue using the microdrive device, without removing the microdrive device from the target site; and recording neural activity at the second target position using said electrodes.

The CCMD allows experimenters to insert electrodes for a period of many days, and then retract the electrodes and reinsert the electrodes in a new location without repeated surgical intervention. The CCMD allows experimenters to place a group of electrodes at a target site in neural tissue and maintain the position of the electrodes across multiple recording sessions, similar to conventional surgically implanted chronic electrodes. CCMD also allows the electrodes to be withdrawn from the neural tissue and repositioned in the manner of conventional inserted acute electrodes. Thus, the CCMD provides advantages taken from conventional techniques without the accompanying limitations of those conventional techniques. There is no apparent limitation to the number of X, Y, Z locations that can be explored within a target site. The reduced size of the CCMD relative to conventional microdrives allows the CCMD to be positioned within a conventional recording chamber. In addition, since the CCMD is designed to be physically compatible with a conventional recording chamber, initial tissue exploration in a target site can be done either with a CCMD or conventional inserted acute electrodes and then the CCMD can be used for chronic neural recording of the acutely identified target area. This flexibility of application improves the yield and efficiency of neural recording.

BRIEF DESCRIPTION OF THE DRAWINGS

FIGS. 8A through 8D show top, side and perspective views of a fine leadscrew.

FIGS. 17A–17H show the same assembly process illustrated in FIGS. 16A–16H from a different perspective.

DETAILED DESCRIPTION

The present disclosure describes methods and apparatus implementing a chronic chamber microdrive ("CCMD") as well as methods of using a CCMD for neural recording. The CCMD provides experimenters with a device and technique for combining chronic and acute neural recording without repeated surgical procedures. A target site is prepared by surgically opening a craniotomy over the target neural tissue and inserting a conventional cylindrical recording chamber into the craniotomy. The CCMD is placed inside the recording chamber while maintaining the chamber seal, and is thus implanted in the skull of the subject. By maintaining the chamber seal, the electrodes can remain in place for extended periods of time, allowing chronic neural recording.

The repositionability of the CCMD provides for acute or chronic neural recording at multiple locations within the site exposed within the recording chamber. The CCMD includes one or more electrodes which are positioned in the x-y plane (generally parallel to the surface of the target site) by a dual non-concentric cylinder mechanism, and in the Z direction (depth) by a combination of a coarse leadscrew and a set of one or more individual fine leadscrews. This dual non-concentric cylinder mechanism provides for a placement of the electrodes in substantially all of the XY positions exposed within the recording chamber.

Figure 1A:
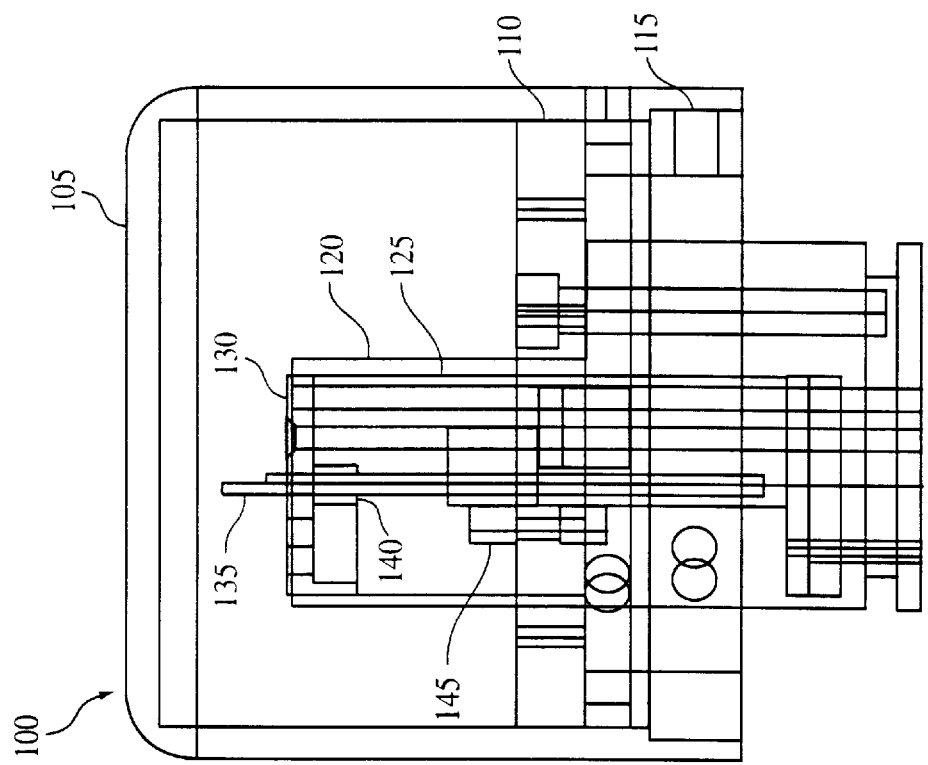
FIGS. 1A through 1D show transparent side, top, and perspective views of a CCMD.
Figure 1B:
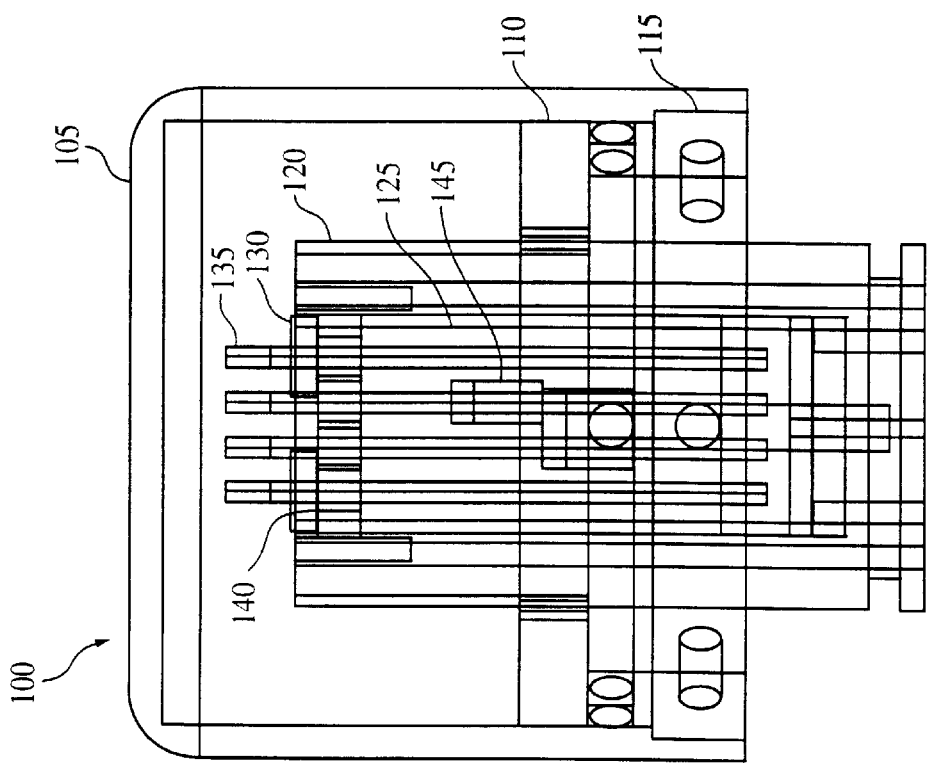
Figure 1D:
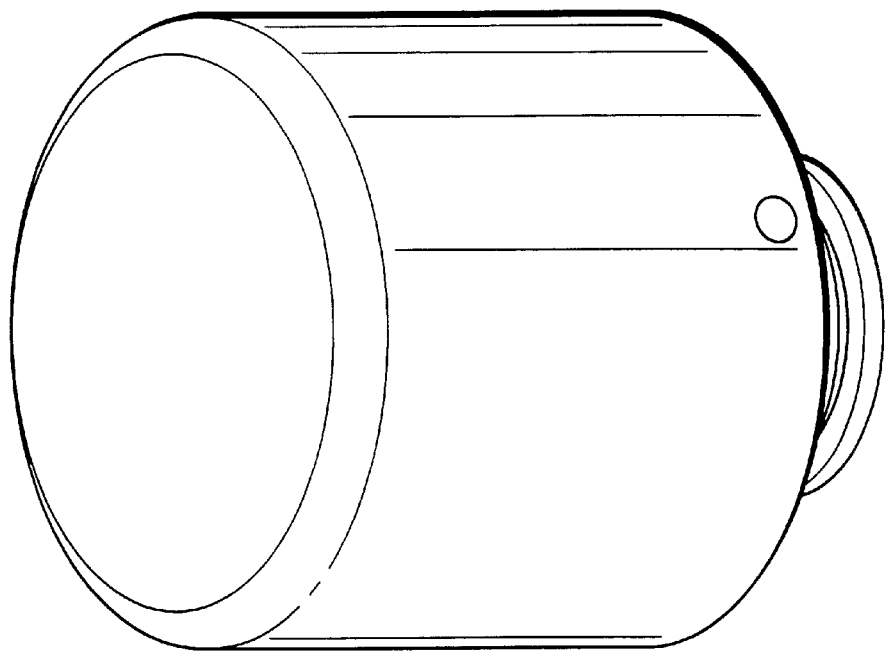
Figure 1C:
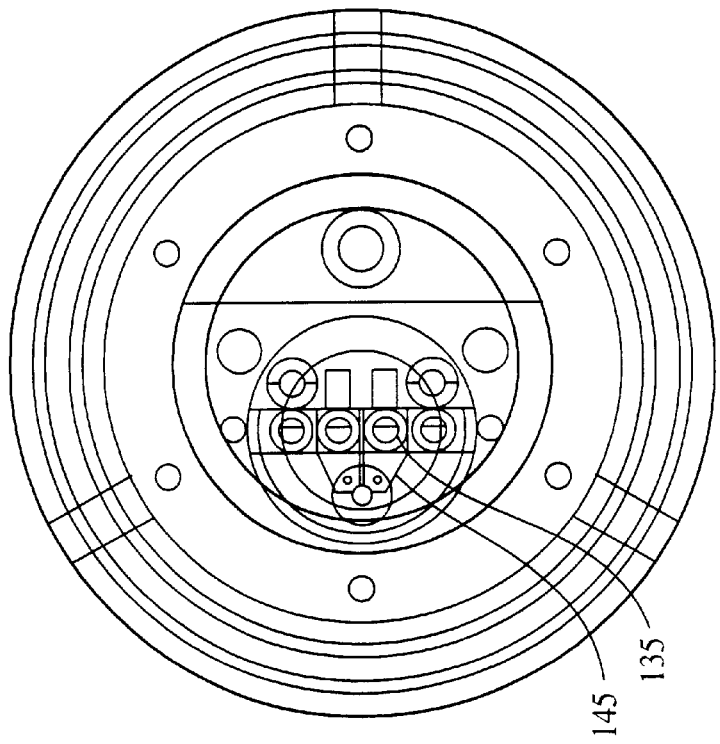
Figure 2A:
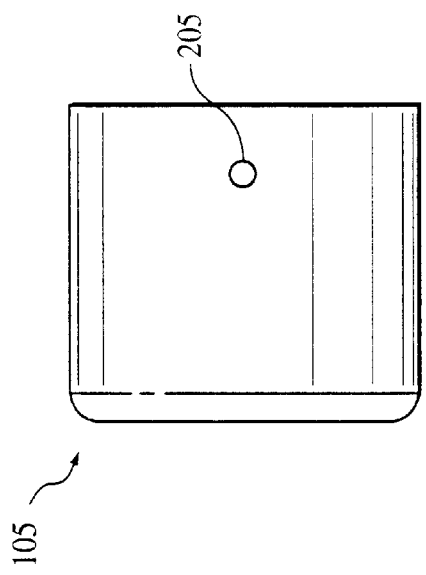
FIGS. 2A through 2D show top, side, and perspective views of the protective cap.
Figure 2B:
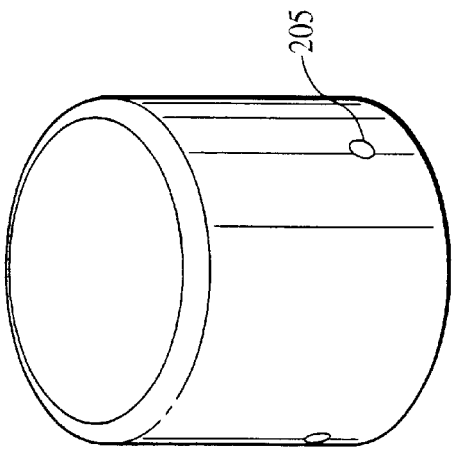
Figure 2C:
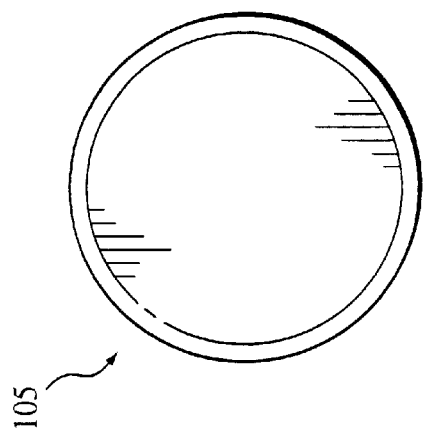
Figure 2D:
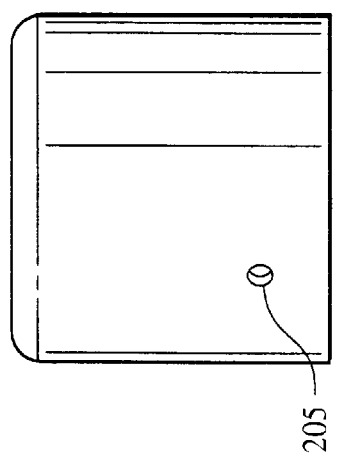
Figure 3B:
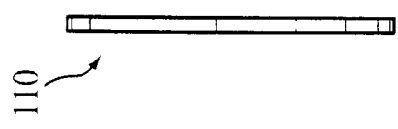
FIGS. 3A through 3D show top, side, and perspective views of the upper plate.
Figure 3D:
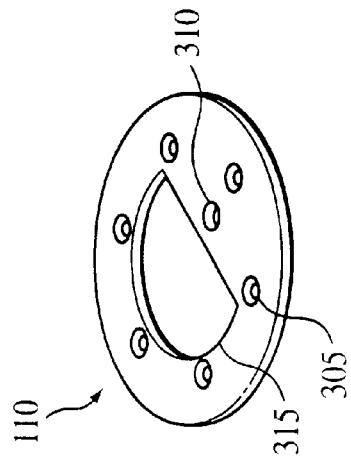
Figure 3A:
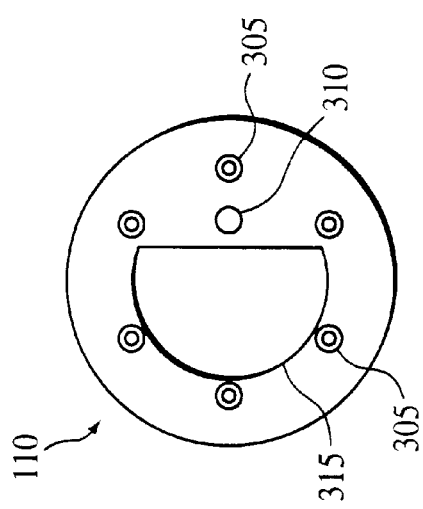
Figure 3C:
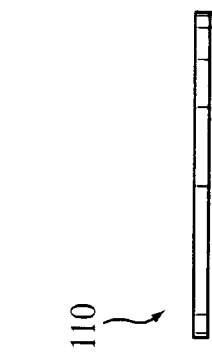
Figure 4B:
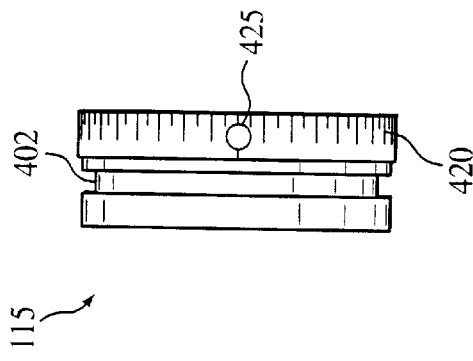
FIGS. 4A through 4D show top, side, and perspective views of the lower plate.
Figure 4D:
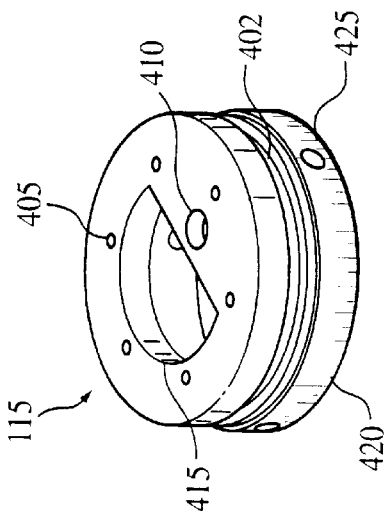
Figure 4A:
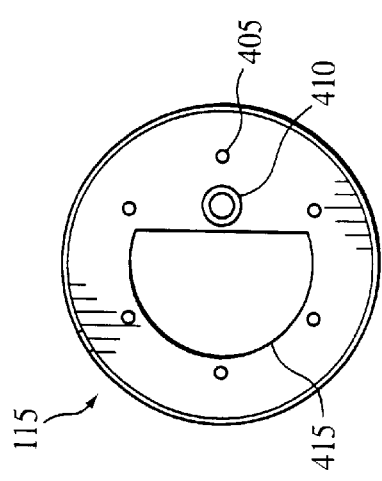
Figure 4C:
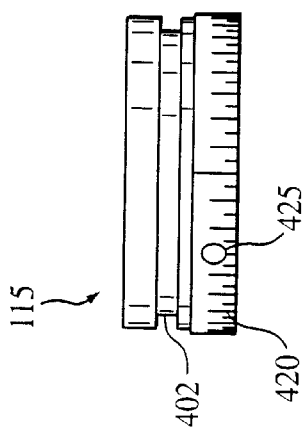

FIGS. 1A through 1D show transparent side, top, and perspective views of a CCMD 100. FIG. 1A shows a front view of the CCMD (where front is arbitrarily determined as a particular facing of the CCMD for differentiation of views only). FIG. 1B shows a side view of the CCMD 100. FIG. 1C shows a top view of the CCMD 100. FIG. 1D shows a perspective view of the CCMD 100.

The CCMD 100 is positioned within the recording chamber within a craniotomy over a target site (not shown). A protective cap 105 covers the CCMD 100. The cap 105 is preferably removed when the CCMD is being used for neural recording. An upper plate 110 is positioned against a lower plate 115. The upper plate 110 and lower plate 115 are aligned and held together by hold-down screws. The lower plate 115 is rotated to provide one degree of freedom for XY positioning. This rotation rotates the entire CCMD 100. A coarse leadscrew (not shown) is positioned in a corresponding passage in the outer cylinder 120. The coarse leadscrew also passes through corresponding openings in the upper plate 110 and lower plate 115 and the head of the coarse leadscrew is captured between the plates 110 and 115. The coarse leadscrew provides coarse positioning in the Z direction for the CCMD 100. An outer cylinder 120 passes through openings in the upper plate 110 and lower plate 115, allowing vertical motion but preventing rotation. An inner cylinder 125 is positioned in a passage in the outer cylinder 120. The inner cylinder 125 provides a second degree of rotational movement by rotating within the outer cylinder 120. The longitudinal axis of the outer cylinder 120 is co-incident with and fixed rotationally to the longitudinal axis of the lower plate 115. The longitudinal axis of the outer cylinder 120 is parallel to but not co-incident with the longitudinal axis of the inner cylinder 125. Thus, the combined rotations of the lower plate 115 and the inner cylinder 125 provide substantially complete access to the available XY positioning area within the recording chamber for electrodes within the inner cylinder 125, as described below. An inner cylinder cap 130 is positioned on the surface of the inner cylinder 125 at the upper end of the passage in the outer cylinder 120. One or more fine leadscrews 135 are positioned in corresponding passages within the inner cylinder 125 and the inner cylinder cap 130. The fine leadscrews 135 provide Z positioning for corresponding electrodes (not shown in FIGS. 1A through 1D).

Each fine leadscrew 135 has a corresponding leadscrew collar 140 fixed to the fine leadscrew 135 and positioned below the inner cylinder cap 130. A leadscrew rider 145 is positioned on a corresponding fine leadscrew 135, such that the corresponding fine leadscrew 135 passes through an opening in the leadscrew rider 145. Each leadscrew rider 145 is preferably coupled to an electrode (not shown) and is used to position the electrode in the Z direction. Stops of each the leadscrew riders 145 extend into corresponding leadscrew rider channels in the inner cylinder 125 for holding the leadscrew riders 145 rotatably in place. As the fine leadscrew 135 turns, the corresponding leadscrew rider 145 moves along the length of the fine leadscrew 135, providing Z positioning for the corresponding electrode. FIGS. 1A through 1D show four configurations of leadscrew riders 145. Each leadscrew rider 145 is configured appropriately to position a corresponding electrode such that the electrodes are aligned with a common guide tube hole in the inner cylinder 125. A guide tube preferably extends through the guide tube hole and out of the bottom of the inner cylinder 125. Various configurations of single or multiple tubes can be used, such as a common guide tube, separate guide tubes for respective electrodes, or a common guide tube enclosing separate guide tubes. The leadscrew riders 145 of the CCMD 100 are preferably configured such that the leadscrew riders 145 move independently of one another and do not interfere with the movement of one another.

The electrodes used for neural recording are preferably fine wire or microwire bundle electrodes, such as tetrodes. However, other types of electrodes are also possible, such as single or multi-wire electrodes. The electrodes can also be replaced by non-electrical probes. The electrodes used are preferably sufficiently flexible to store slack within the device to allow for the desired range of positioning. Connections to the electrode wires are preferably provided by miniature electrical connectors. The spacing between the electrodes can vary depending upon the application, such as approximately 200 microns for efficient neural recording coverage. The electrodes are preferably connected to electrical connection components positioned on the upper plate 110 (not shown in FIGS. 1A–1D). These electrical connection components are used for neural recording through the electrodes introduced to the neural tissue. Alternatively, the electrodes can be connected to electrical components external to the CCMD 100.

A conventional recording chamber is typically approximately 19 mm in external diameter and approximately 17 mm in internal diameter. These dimensions are representative of the recording chambers manufacturer's design. While these dimensions do not necessarily limit the design and configuration of the CCMD, the dimensions do determine an available space for compatibility with present recording chamber design. For example, in one implementation of the CCMD, the CCMD includes four leadscrews for Z positioning. The number of leadscrew drivers for Z positioning is dependent upon the application and may be limited by size constraints of the leadscrew rider design as well as the design of other components. The range of the Z positioning is limited by the acceptable height of the CCMD according to the application. In a preferred implementation of CCMD, a range limit of approximately 5 mm for coarse positioning and approximately 15 mm for fine positioning is selected as a generally convenient range.

Thus, the dimensions of the recording chamber to be used with the CCMD determine the available XY, positioning area. In one implementation, the available XY positioning area is a circle approximately 2 mm smaller in diameter than the inner diameter of the recording chamber. Within this XY positioning area, there is no inherent limits to positioning resolution. The dual non-concentric cylinder design and the O-ring seals for the recording chamber can limit the XY, positioning area. However, changes in material technology, such as allowing a thinner sealing member to be used rather than the O-ring or using self-sealing materials eliminating the need for an O-ring, can increase the overall available XY positioning area.

FIGS. 2 through 11 show detailed views of preferred configurations of various components for a preferred implementation of the CCMD 100. Various components of the CCMD 100 include one or more holes for receiving various screws, such as hold-down screws and set screws. The number of holes in these components correspond between components where appropriate, and may vary from one to any other appropriate number, depending upon the application. In addition, the screws themselves are not shown in the figures for clarity.

FIGS. 2A through 2D show top, side, and perspective views of the protective cap 105. The protective cap 105 is preferably made from a smooth material such as brass. The inner diameter of the protective cap 105 is preferably larger than the outer diameter of each of the components of the CCMD 100 to provide complete coverage of the CCMD 100 at appropriate times. The protective cap 105 can be held in place by friction or latching mechanisms or by screws. The protective cap 105 preferably includes set screw holes 205 to hold the protective cap 105 in place against the lower plate 115. The protective cap 105 is removed to position the CCMD 100 and for recording. The protective cap is preferably left on, covering the CCMD 100, when the electrodes do not need to be positioned, such as when neural recording is not being performed.

FIGS. 3A through 3D show top, side, and perspective views of the upper plate 110. The upper plate 110 is preferably a disc made from a smooth metal such as brass. The upper plate 110 includes one or more hold-down screw holes 305 for aligning and holding the upper plate 110 in place against the lower plate 115. The upper plate 110 also includes a coarse leadscrew access hole 310 for providing passage to a tool (not shown) to adjust the coarse leadscrew. The hold-down screw holes 305 are preferably beveled to accommodate heads of corresponding hold-down screws (not shown). The inner plate 110 includes a passage 315 for aligning the upper plate 110 with the outer cylinder 120. The passage 315 is preferably partially circular with a straight edge to promote joint rotation of the entire CCMD 100 with the outer fcylinder 120.

FIGS. 4A through 4D show top, side, and perspective views of the lower plate 115. The lower plate 115 is preferably made from a smooth material such as brass. The lower plate is a cylinder of varying diameters. The variation in diameter forms a set screw indention 402 providing shoulders for the set screws for the protective cap 105. The lower plate 115 includes hold-down screw holes 405 for receiving hold-down screws to hold the upper plate 110 in place against the lower plate 115. The lower plate 115 also includes a coarse leadscrew hole 410 for receiving the coarse leadscrew. The lower plate 115 includes a passage 415 of substantially the same shape configuration as the passage 315 in the upper plate 110. This passage 415 is also for receiving the outer cylinder 120. The edge of the passage 415 forms a ledge within the lower plate 115 which contacts the outer cylinder 120 and restricts the extension of the outer cylinder 120 through the lower plate 115. Graduation marks 420 are preferably placed around the perimeter of at least a portion of the lower plate 115 for controlling the amount of rotation applied to the lower plate 115. The graduation marks 420 are externally visible when the protective cap 105 is removed from the CCMD 100. The lower plate 115 also includes chamber set screw holes 425 for receiving chamber set screws for holding the lower plate 115 in place (rotatably) against the recording chamber.

Figure 5B:
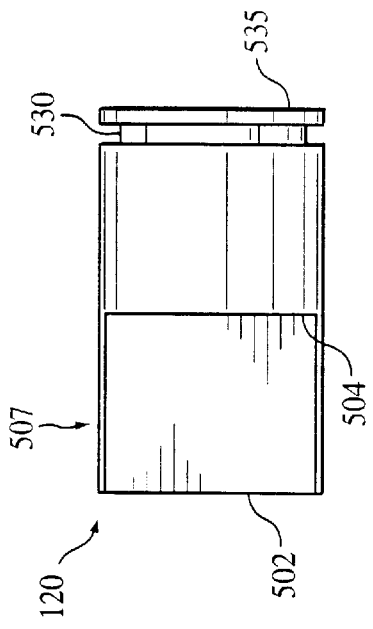
FIGS. 5A through 5D show top, side, and perspective views of the outer cylinder.
Figure 5D:
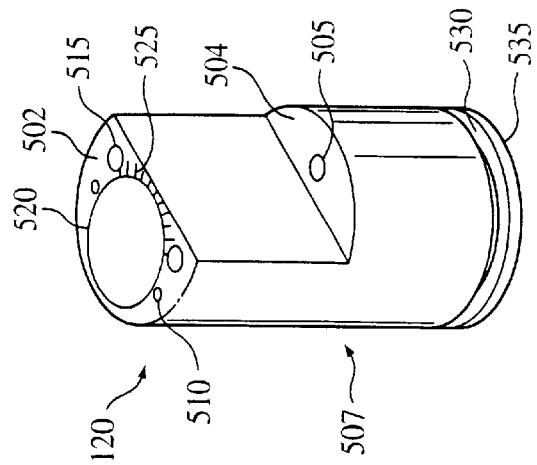
Figure 5A:
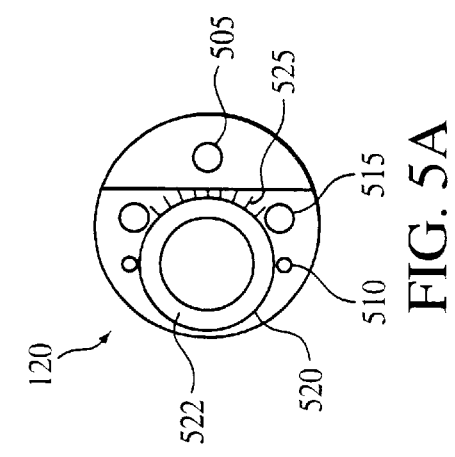
Figure 5C:
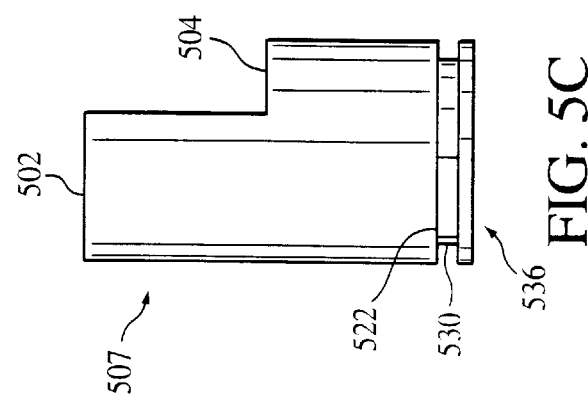
Figure 6B:
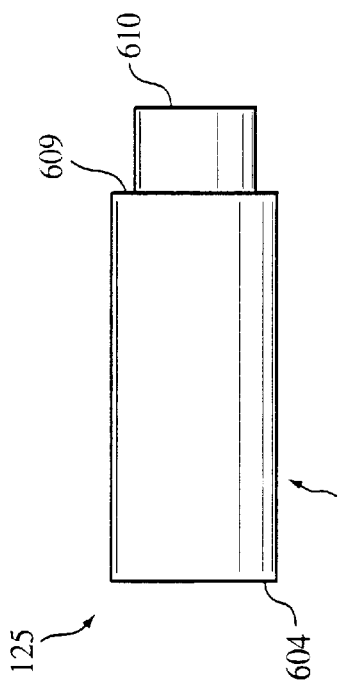
FIGS. 6A through 6D show top, side, and perspective use of the inner cylinder.
Figure 6A:
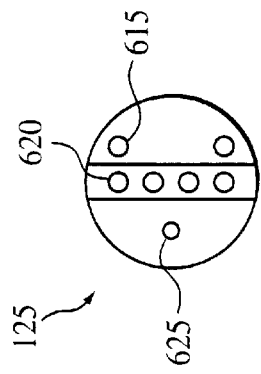
Figure 6D:
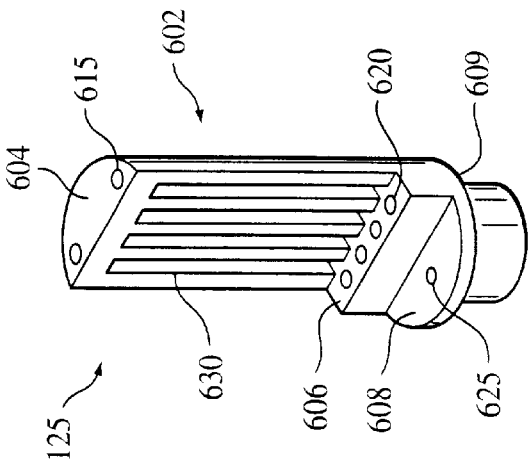
Figure 6C:
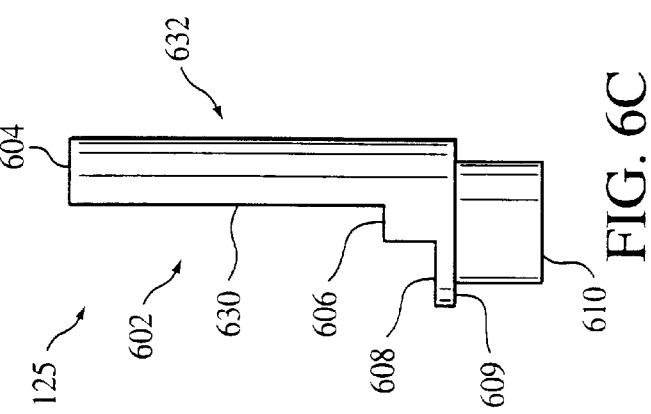
Figure 7B:
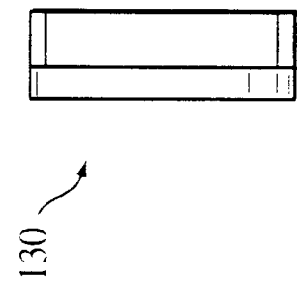
FIGS. 7A through 7D show top, side, and perspective views of the inner cylinder cap.
Figure 7D:
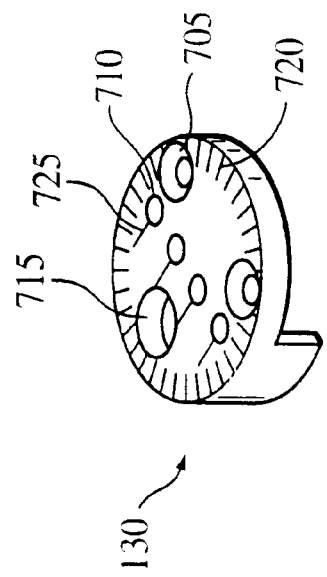
Figure 7A:
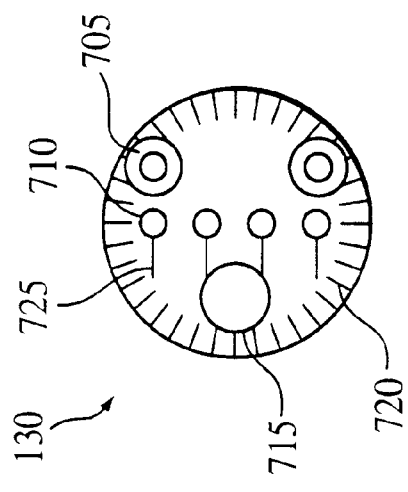
Figure 7C:
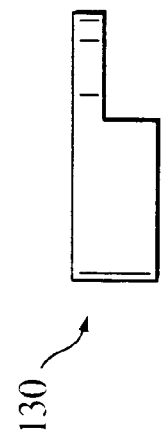
Figure 9B:
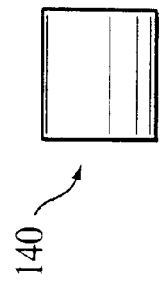
FIGS. 9A through 9D show top, side and perspective views of a leadscrew collar.
Figure 9D:
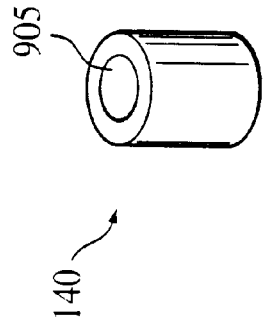
Figure 9A:
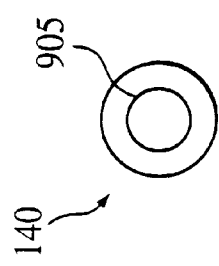
Figure 9C:
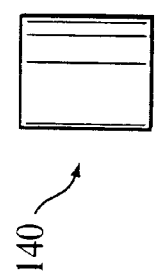
Figure 10A:
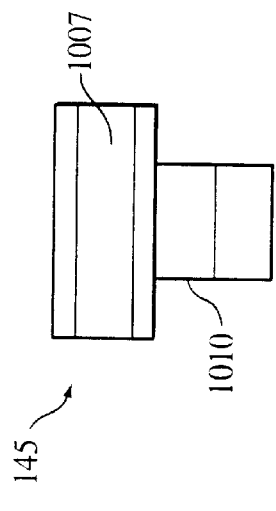
FIGS. 10A through 10D show top, side and perspective views of one configuration of a leadscrew rider.
Figure 10B:
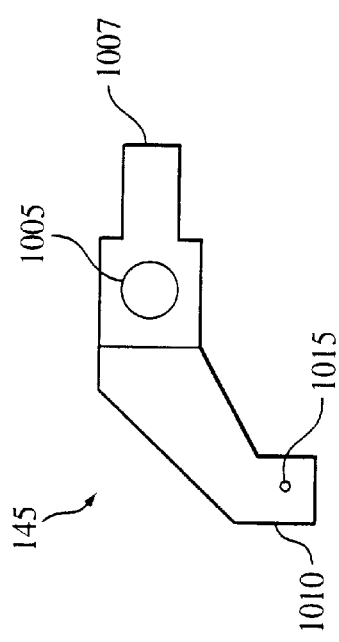
Figure 10C:
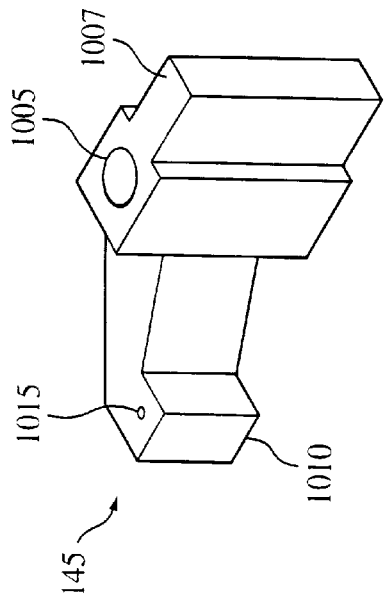
Figure 10D:
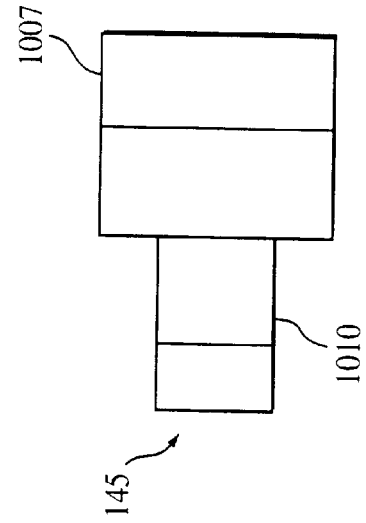
Figure 11A:
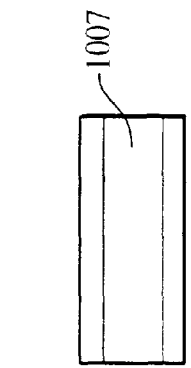
FIGS. 11A through 11D show top, side and perspective views of an alternative configuration of a leadscrew rider.
Figure 11B:
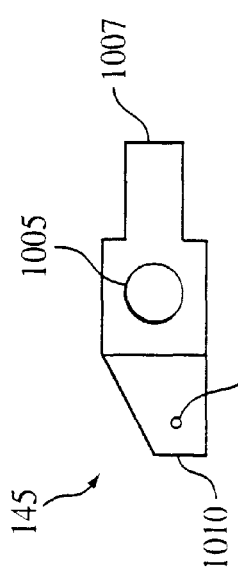
Figure 11C:
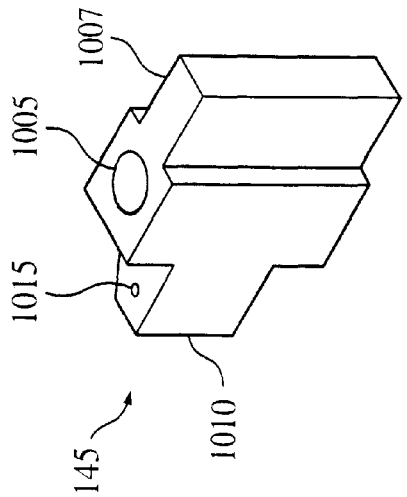
Figure 11D:
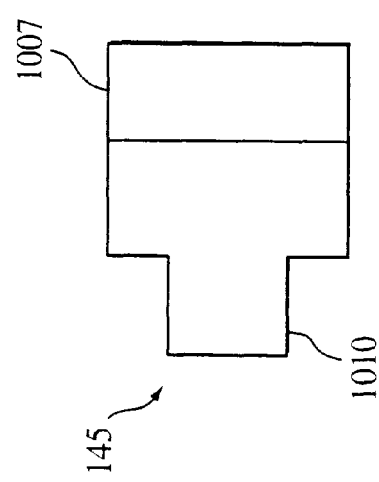

FIGS. 5A through 5D show top, side, and perspective views of the outer cylinder 120. The outer cylinder 120 is preferably made from a monolith of smooth material such as 303 stainless steel. The outer cylinder 120 has an overall cylindrical shape with a section on one side cut away forming a generally "L"-shaped side perspective as shown in FIG. 5C. A portion 507 of the outer cylinder 120 forming the upper part of the L shape forms a shape conforming to the passages 315 and 415 in the upper plate 110 and lower plate 115, respectively. This conforming shape serves to promote the joint rotation of the plates 110, 115 and the outer cylinder 120. The portion 507 also defines an first upper surface 502 and a second upper surface 504. The outer cylinder 120 includes a coarse leadscrew hole 505 in the second upper surface 504 for receiving the coarse leadscrew for gross Z positioning. The coarse leadscrew 505 preferably does not completely penetrate through the outer cylinder 120.

The first upper surface 502 of the outer cylinder 120 includes clamp down screw holes 510 for receiving clamp down screws (not shown). The clamp down screws have wide heads which extend over the top of the inner cylinder. When a desired position for the inner cylinder 125 has been achieved, the clamp down screws are tightened and the bottoms of the heads press against the top of the inner cylinder 125, holding the inner cylinder 125 fixed rotationally. The outer cylinder 120 includes flush holes 515 which penetrate through the upper surface 502 completely through the outer cylinder 120. The flush holes 515 can be used to flush a void between the bottom of the CCMD 100 and the upper surface of the dura with an appropriate liquid or to deliver antibiotics or other treatments to the target site tissue. The flush holes 515 are preferably sealed using screws (not shown) or wax (not shown).

Figure 13D:
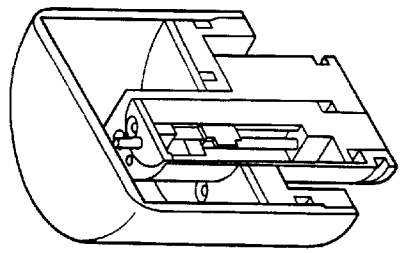
FIGS. 13A through 13O show progressive sectional views of a CCMD where each figure shows a view progressively moved along an arbitrary Y axis.
Figure 13C:
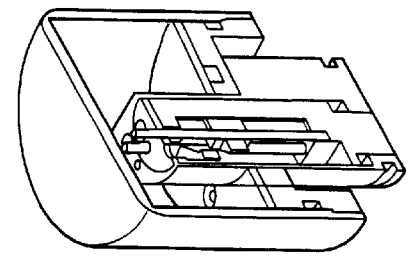
Figure 13B:
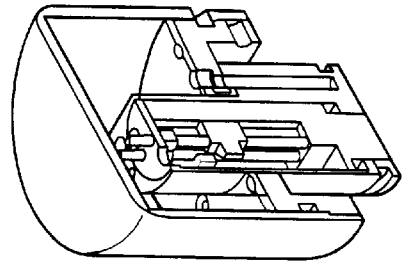
Figure 13A:
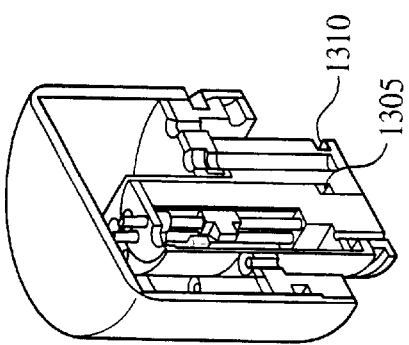
Figure 13H:
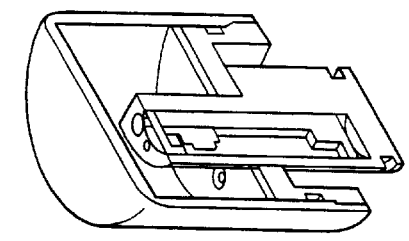
Figure 13G:
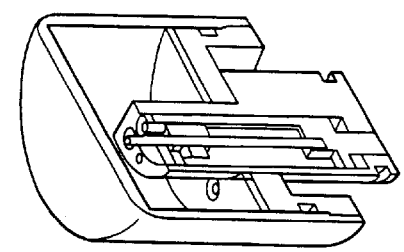
Figure 13F:
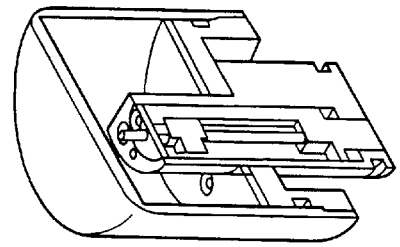
Figure 13E:
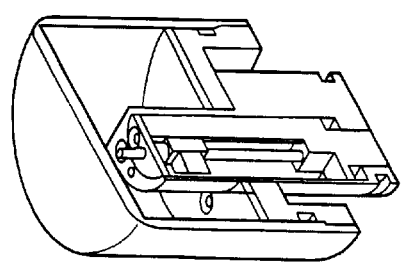
Figure 13L:
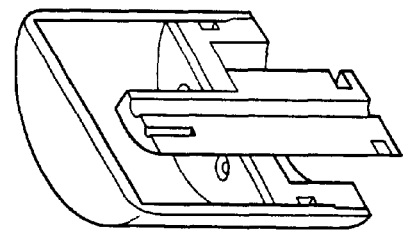
Figure 13K:
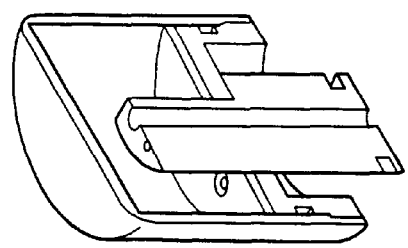
Figure 13J:
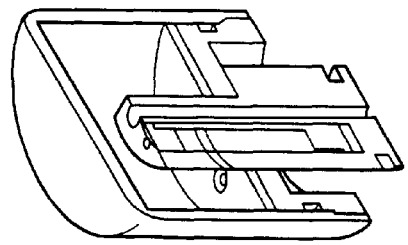
Figure 13I:
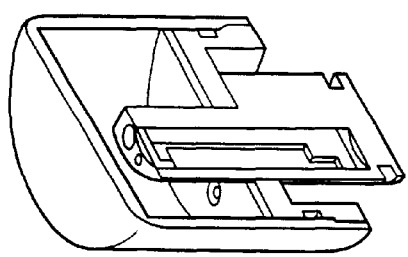
Figure 13O:
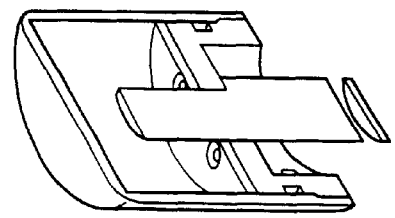
Figure 13N:
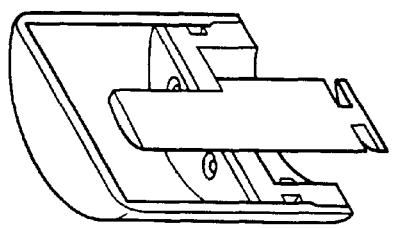
Figure 13M:
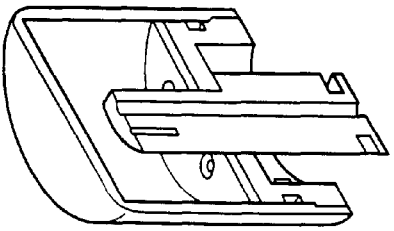
Figure 14D:
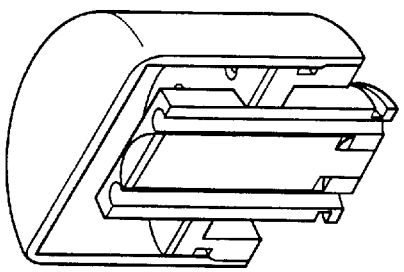
FIGS. 14A through 14O show progressive sectional views of the same CCMD progressing along an X axis perpendicular to the Y axis as FIGS. 13A through 13O.
Figure 14H:
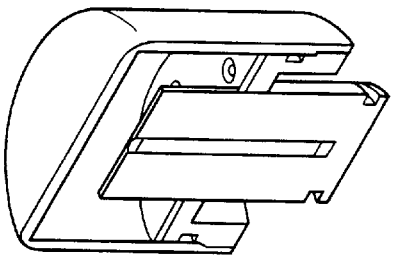
Figure 14C:
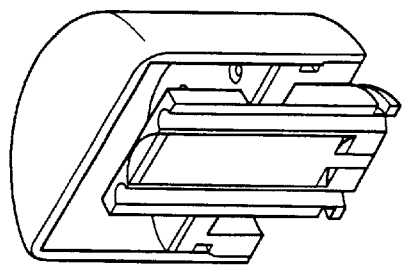
Figure 14G:
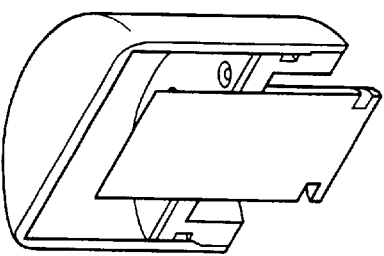
Figure 14B:
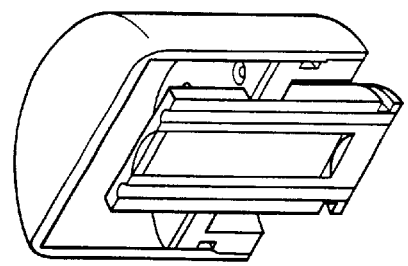
Figure 14F:
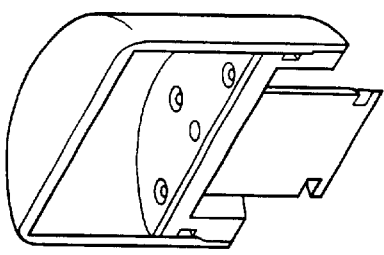
Figure 14A:
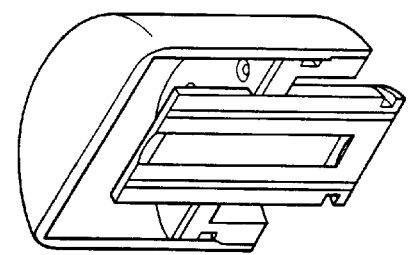
Figure 14E:
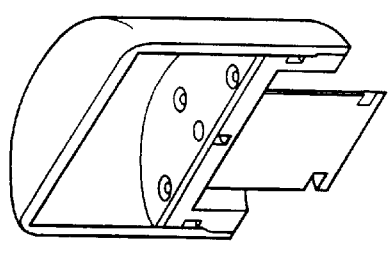
Figure 14L:
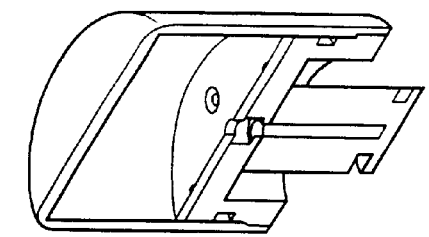
Figure 14K:
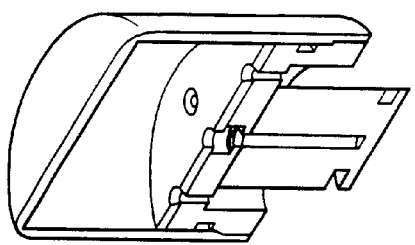
Figure 14J:
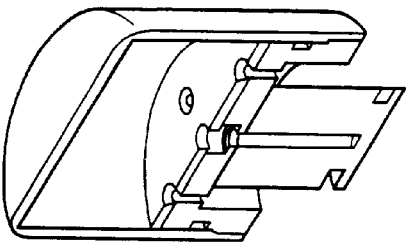
Figure 14I:
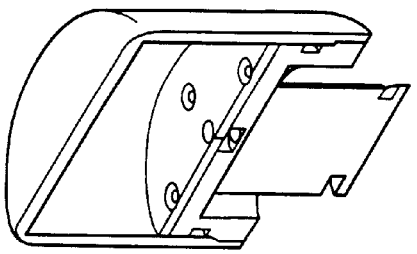
Figure 14O:
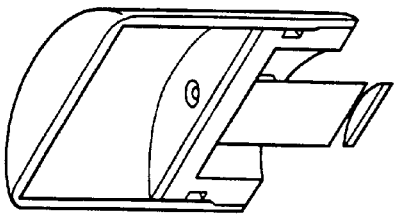
Figure 14N:
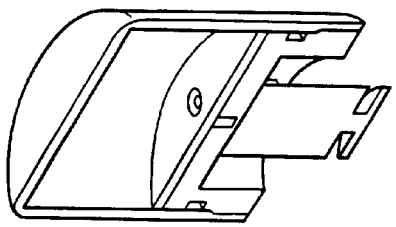
Figure 14M:
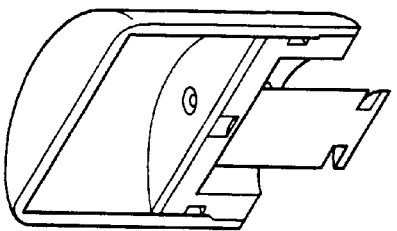
Figure 15D:
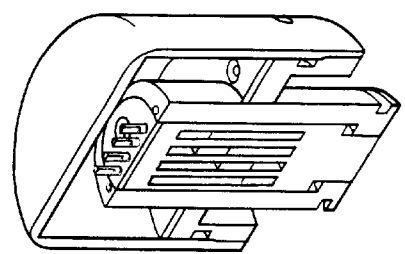
FIGS. 15A through 15O show progressive sectional views of the CCMD taken along the same X axis as in FIGS. 14A through 14O, but in the opposite direction from the progression in FIGS. 14A through 14O.
Figure 15H:
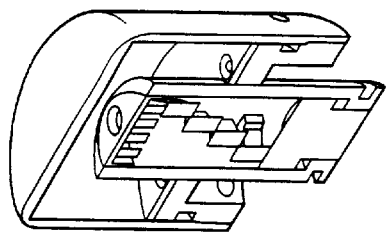
Figure 15C:
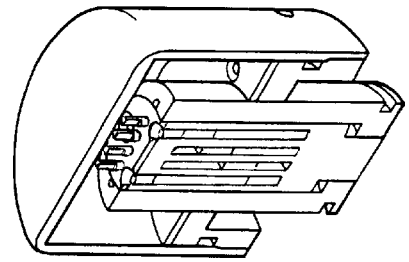
Figure 15G:
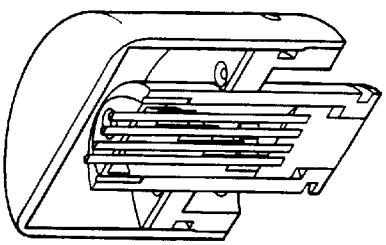
Figures 15A, 15B:
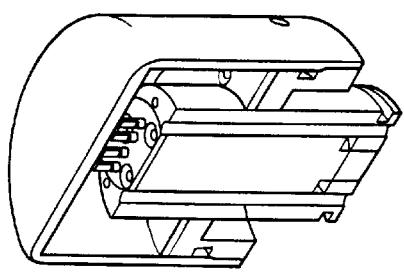
Figures 15E, 15F:
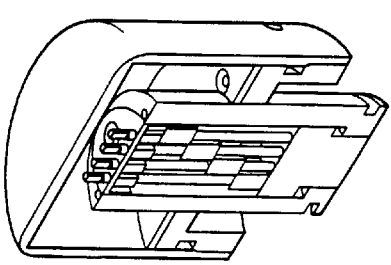
Figure 15L:
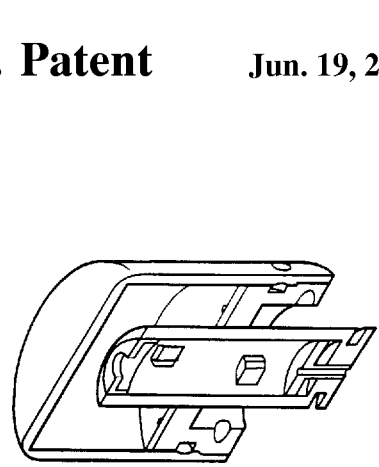
Figure 15K:
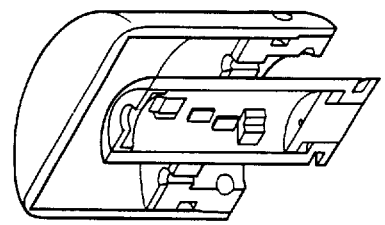
Figure 15J:
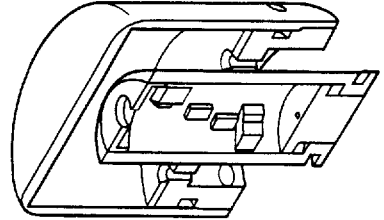
Figure 15I:
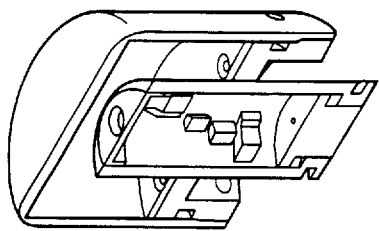
Figure 15O:
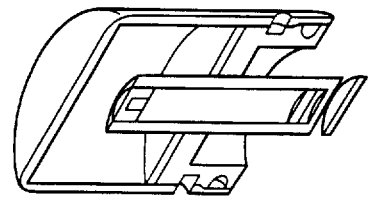
Figure 15N:
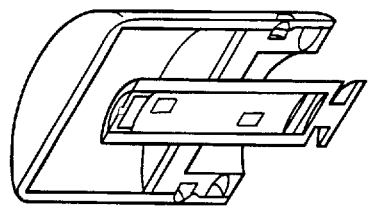
Figure 15M:
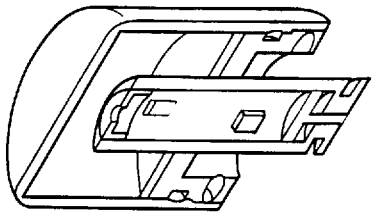

The outer cylinder 120 also includes a bi-level passage 520 for receiving and vertically positioning the inner cylinder 125. The bi-level nature of the passage 520 forms a ledge 522 which provides a stable seat for the inner cylinder 125 in the passage 520. The ledge 522 also forms the bottom of an inner cylinder sealing member channel (see inner cylinder sealing member channel 1305 in FIG. 13A). The outer side of the inner cylinder sealing member channel is formed by the passage 520. The inner side and top of the inner cylinder sealing member channel are formed by the bottom of the inner cylinder 125. The passage 520 is substantially round such that the inner cylinder 125 is free to rotate within the passage 520. The passage 520 penetrates from the upper surface 502 of the outer cylinder 120 completely through the outer cylinder 120. The upper surface 502 of the outer cylinder 120 includes graduation marks 525 around at least a portion of the edge of the passage 520. The graduation marks 525 form a vernier scale with graduation marks on inner cylinder cap 130 (see graduation marks 720 in FIG. 7A) and are used in controlling the amount of rotation of the inner cylinder 125 positioned in the passage 520. The outer cylinder 120 includes an outer cylinder sealing member channel 530 for receiving a sealing member such as an O-ring (see outer cylinder sealing member channel 1310 in FIG. 13A). A lower surface 535 of the outer cylinder 120 opposite to the upper surfaces 502 and 504, nearer in operation to the target site and exposed to the tissue of the target site, is preferably a polished surface.

FIGS. 6A through 6D show top, side, and perspective use of the inner cylinder 125. The inner cylinder 125 is preferably formed from a monolith of smooth material such as 303 stainless steel. An upper portion 602 of the inner cylinder 125 is partially cut away to form a tri-level upper surface including a first upper surface 604, a second upper surface 606, and a third upper surface 608. A lower surface 609 of the upper portion 602, opposite the upper surfaces 604, 606, 608, forms a ledge which provides the upper side of the inner cylinder sealing member channel, as described above. A lower surface 610 of the inner cylinder 125 is preferably polished and is exposed to the tissue of the target site. The upper surface 604 of the inner cylinder 605 includes hold-down screw holes 615 for receiving hold-down screws to hold the inner cylinder cap 130 in place against the upper surface 604 of the inner cylinder 135. The second upper surface 606 of the inner cylinder 125 includes leadscrew holes or bearings 620 for receiving fine leadscrews 135. The fine leadscrew bearings 620 preferably do not penetrate through the inner cylinder 125.

The third upper surface 608 includes a guide tube hole 625 for receiving a guide tube (not shown). As noted above, the guide tube is for receiving the electrodes. The guide tube hole 622 completely penetrates from the third upper surface 608 through the inner cylinder 125. In operation, the guide tube is inserted into the guide tube hole 622 and extends below the lower surface 610 of the inner cylinder 125. The guide tube is press or friction fit into the guide tube hole 625 and optionally also held in place by an adhesive. As the inner cylinder 125 is lowered in the Z direction towards the tissue of the target site by advancement of the coarse leadscrew, the guide tube penetrates the dura and allows for the electrodes to enter the relatively softer neural tissue underneath. The electrodes emerge from the guide tube into the neural tissue by advancement of the fine leadscrews 135.

The inner cylinder 125 includes one or more leadscrew rider channels 630 in a portion 632 of the inner cylinder between the first upper surface 604 and the second upper surface 606. The leadscrew rider channels 630 are for receiving stops of corresponding leadscrew riders 145. The leadscrew rider channels 630 hold the leadscrew riders 145 substantially rotatably in place in the XY plane, while allowing the leadscrew riders 145 to move in the Z direction. Thus, through the interaction of threading on a fine leadscrew 135 and the corresponding leadscrew rider 145 and being held rotatably in place by the leadscrew rider channel 630, the leadscrew rider 145 translates along the fine leadscrew 135 in the Z direction. The length of the leadscrew rider channels 630 defines the range of Z movement of the leadscrew riders 145 and hence the electrodes attached thereto. The number of leadscrew bearings 620 corresponds to the number of fine leadscrews 135 and hence the number of electrodes used in the neural recording session. In alternative implementations, the relative heights and number of upper surfaces in the inner cylinder 125 can vary.

FIGS. 7A through 7D show top, side, and perspective views of the inner cylinder cap 130. The inner cylinder cap 130 is preferably made from a monolith of smooth material such as brass. The inner cylinder cap 130 includes hold-down screw holes 705 for receiving hold-down screws to hold the inner cylinder cap 130 in place against the inner cylinder 125. The hold-down screw holes 705 are preferably beveled to accommodate heads of corresponding hold-down screws (not shown). The inner cylinder cap 130 includes leadscrew locator holes 710 to allow an upper portion of a corresponding fine leadscrew 135 to protrude from the inner cylinder 125 through the inner cylinder cap 130 for controlling rotation of the fine leadscrew 135. The inner cylinder cap 130 includes a passage 715 to allow passage of electrical connections to the electrodes held in the leadscrew riders 145 between the inner cylinder cap 130 and the inner cylinder 125. The inner cylinder cap 130 is marked with graduation marks 720 for controlling the rotation of the inner cylinder 125. The inner cylinder cap 130 is also marked with zero-position marks 725 next to each of the leadscrew locator holes 710. The zero-position marks 725 are used to indicate the relative rotation of the fine leadscrews 135 protruding through the leadscrew locator holes 710.

FIGS. 8A through 8D show top, side and perspective views of a fine leadscrew 135. The fine leadscrew 135 is preferably made from a smooth material such as 303 stainless steel. The fine leadscrew 135 includes an upper portion 802 and a lower portion 804. The upper portion 802 includes a cutaway forming a ledge 805 delimiting the juncture of the upper portion of 802 and the lower portion 804. The non-circular shape of the upper portion 802 of the fine leadscrew 135 allows for rotation of the fine leadscrew 135 using a socket-type leadscrew tool matched to the shape of the upper portion 802, as described below in FIGS. 12A–12H. At least a portion of the upper portion 802 of the fine leadscrew 135 protrudes through the corresponding leadscrew hole in the inner cylinder cap 130. Alternative configurations of the upper portion 802 of the fine leadscrew 135 are possible when used in conjunction with a corresponding leadscrew tool which is capable of rotating the fine leadscrew 135. The lower portion 804 of the fine leadscrew 135 is preferably threaded. As described above, this threading operates to adjust the Z position of a corresponding leadscrew rider 145.

FIGS. 9A through 9D show top, side and perspective views of a leadscrew collar 140. The leadscrew collar 140 is a cylindrical ring preferably made from a smooth material such as 303 stainless steel. The leadscrew collar 140 is preferably thread locked to the corresponding fine leadscrew 135 and preferably acts as a thrust bearing for the fine leadscrew 135. Thus, an inner surface 105 of the leadscrew collar 140 is threaded to match the threading of the corresponding fine leadscrew 135. In an alternative implementation, the leadscrew collars 140 may be omitted or may be formed as an integral part of the fine leadscrews 135.

FIGS. 10A through 10D show top, side and perspective views of one configuration of a leadscrew rider 145. The leadscrew rider 145 is preferably made from a smooth material such as brass and preferably polished to a very smooth finish. The leadscrew rider 145 includes a leadscrew hole 1005 for receiving a corresponding fine leadscrew 135. The leadscrew hole 1005 is threaded to match the threading on the fine leadscrew 135. The fine leadscrew 135 passes through the leadscrew hole 1005. The leadscrew rider 145 includes a stop 1007. The stop 1007 is positioned within a corresponding leadscrew rider channel in the inner cylinder 135, recall leadscrew rider channel 630 in FIGS. 6A through 6D. Through contact between the stop 1007 and the end of the leadscrew rider channel 630, the XY motion and range of Z motion of the leadscrew rider 145 is appropriately constrained.

As the fine leadscrew 135 rotates, the leadscrew rider 145 begins to rotate with the fine leadscrew 135. However, the contact between the stop 1007 and the leadscrew rider channel of the inner cylinder 125 prevents the leadscrew rider 145 from rotating. As a result, the matched threading of the fine leadscrew 135 and the leadscrew hole 1005 translates the rotational motion of the fine leadscrew 135 into linear motion of the leadscrew rider 145 in the Z direction along the length of the fine leadscrew 135. This motion provides for the Z positioning of the electrode held by the leadscrew rider 145.

The leadscrew rider 145 includes an arm portion 1010. The arm portion 1010 includes an electrode hole 1015. The electrode hole 1015 preferably includes a countersink at one or both ends of the electrode hole 1015. The electrode hole 1015 completely penetrates the leadscrew rider 145. The electrode hole 1015 is for receiving an electrode (not shown) for neural recording. The electrode is inserted through the electrode hole 1015 and the electrode hole 1015 is backfilled with an adhesive such as wax or removable glue to hold the electrode in place. The arm portion 1010 is configured to position the electrode hole 1015, and hence the corresponding electrode, in alignment with the guide tube hole of the inner cylinder 125, recall guide tube hole 625 shown in FIGS. 6A through 6D. Thus, the arm portion 1010 provides a connection between the motion of the fine leadscrew 135 and the electrode position over the guide tube hole 625.

The configuration of the arm portion 1010 shown in FIGS. 10A through 10D represents one possible configuration of a leadscrew rider 145 to accommodate a particular configuration of fine leadscrews 135 and inner cylinder 125. Thus, as shown more clearly in FIGS. 1, 13, and 14, in a preferred implementation including 4 fine leadscrews 135 and corresponding leadscrew riders 145, one leadscrew rider 145 is configured as shown in FIGS. 10A through 10D and another leadscrew rider is configured as a mirror image of the configuration shown in FIGS. 10A through 10D. Alternatively, the leadscrew rider 145 can be configured so that the mirror image leadscrew rider 145 is an identical leadscrew rider 145 which is turned over.

FIGS. 11A through 11D show top, side and perspective views of an alternative configuration of a leadscrew rider 145. The leadscrew rider 145 shown in FIGS. 11A through 11D is generally the same as the leadscrew rider 145 shown on FIGS. 10A through 10D, however, the arm portion 1010 is configured differently to position the electrode hole 1015 in a different position. Varying configuration of leadscrew riders 145, such as those shown in FIGS. 10A through 10D and 11A through 11D as well as their corresponding mirror images, are used to position an appropriate number of electrodes in alignment with the guide tube hole 625 of the inner cylinder 125. The configuration of the arm portion 1010 of the leadscrew riders 145 are preferably designed such that each of the leadscrew riders 145 operates independently from each other and does not limit the positioning of other leadscrew riders 145. An alternative implementations, the leadscrew riders 145 can be implemented to operate as limits on the positioning as other leadscrew riders 145.

FIGS. 12A through 12H show top, side and perspective views at different levels of magnification of a preferred leadscrew tool 1200 to be used to rotate fine leadscrew 135. The leadscrew tool 1200 includes a handle 1205, a shaft 1210 and a tip portion 1215. The handle 1205 is preferably knurled to provide improved grip for rotation. A portion of the handle 1215 is preferably cut away to produce a generally circular cross section with one straight side 1220. This straightened side 1220 provides a gross alignment mark.

Figure 12A:
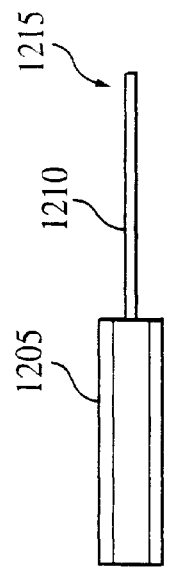
FIGS. 12A through 12H show top, side and perspective views at different levels of magnification of a preferred leadscrew tool to be used to rotate fine leadscrew.
Figure 12B:
Figure 12D:
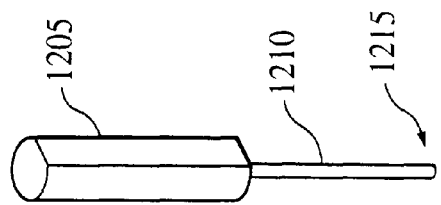
Figure 12C:
Figure 12F:
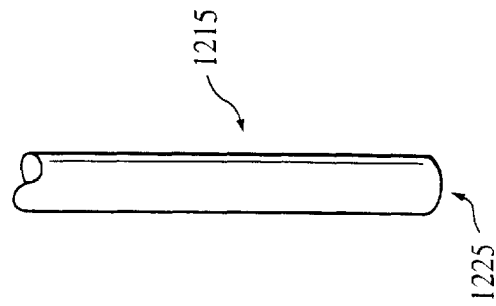
Figure 12H:
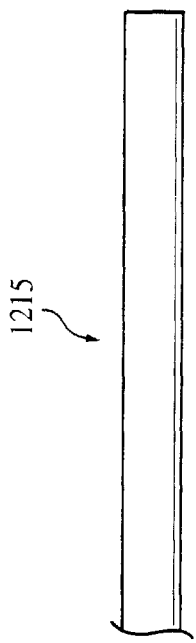
Figure 12E:
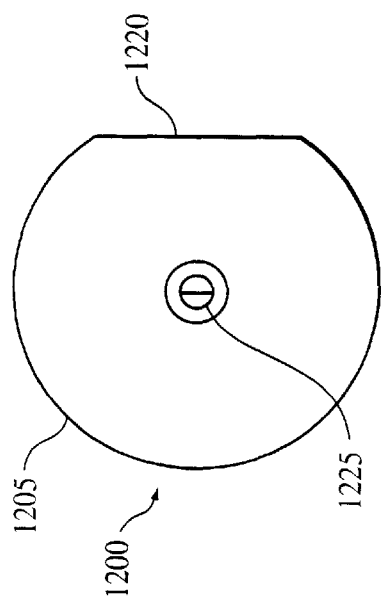
Figure 12G:
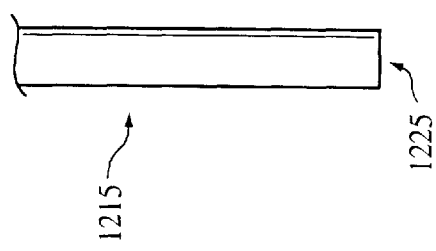

FIGS. 12E though 12H show magnified views of the tip portion 1215 of the leadscrew tool 1200. The tip portion 1215 includes an opening 1225 at the end of the tip 1215. The opening 1225 is a depression penetrating into the tip portion 1215 of the leadscrew tool 1200 and is configured to match the upper portion of the fine leadscrew 135 which protrudes through the leadscrew locator hole of the inner cylinder cap 130, recall leadscrew locator hole 710 in FIGS. 7A through 7D and upper portion 802 of the fine leadscrew 135 in FIGS. 8A through 8D. The tip portion 1215 also includes graduation marks (not shown) along the perimeter of the tip portion to be used in controlling the rotation of the fine leadscrew in coordination with the zero position mark 725 of the inner cylinder cap 130, shown in FIG. 7A through 7D. In alternative implementations, the leadscrew tool 120 can be configured in numerous possible ways, where an opening is provided to match the configuration of the upper portion 802 of the fine leadscrews 135, as shown in FIGS. 8A through 8D. Alternatively, the upper portions 802 of the fine leadscrews 135 can be rotated by an automatic device such as an electric or hydraulic motor.

FIGS. 13, 14 and 15 show progressive sectional views of an assembled CCMD of a preferred implementation (electrodes, guide tubes, electrical connections, and sealing members are omitted for clarity). FIGS. 13A through 13O show progressive sectional views of a CCMD where each figure shows a view progressively moved along an arbitrary Y axis. In FIG. 13A, the inner cylinder sealing member channel 1305 and the outer cylinder sealing member channel 1310 are pointed out. FIGS. 14A through 14O show progressive sectional views of the same CCMD progressing along an X axis perpendicular to the Y axis as FIGS. 13A through 13O. FIGS. 15A through 15O show progressive sectional views of the CCMD taken along the same X axis as in FIGS. 14A through 14O, but in the opposite direction from the progression in FIGS. 14A through 14O.

Figure 16D:
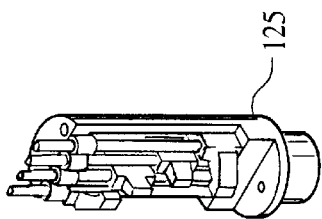
FIGS. 16A through 16H show perspective views of a preferred process of assembling a CCMD.
Figure 16C:
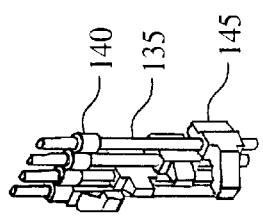
Figure 16B:
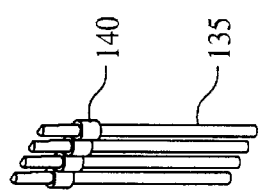
Figure 16A:
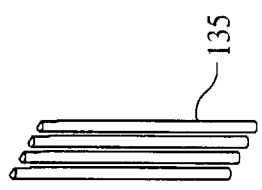

FIGS. 16A through 16H show perspective views of a preferred process of assembling a CCMD. FIG. 16A shows four fine leadscrews 135. In FIG. 16B, leadscrew collars 140 are affixed to each fine leadscrew 135. In FIG. 16C, leadscrew riders 145 of varying configurations are affixed to corresponding fine leadscrews 135 below the leadscrew collars 140.

Figure 16H:
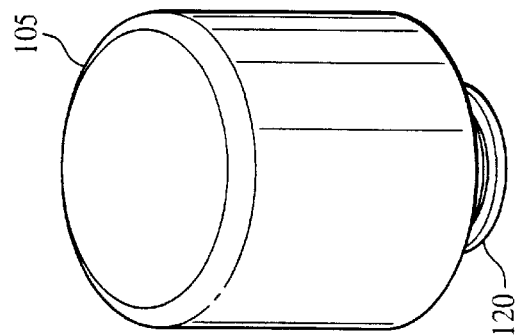
Figure 16G:
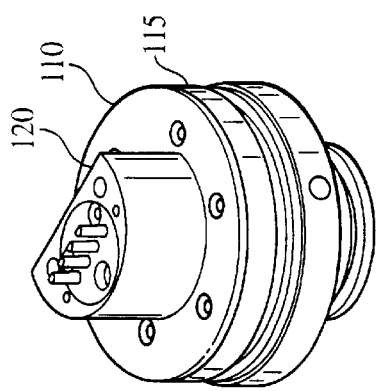
Figure 16F:
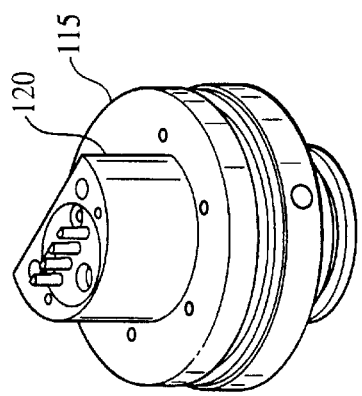
Figure 16E:
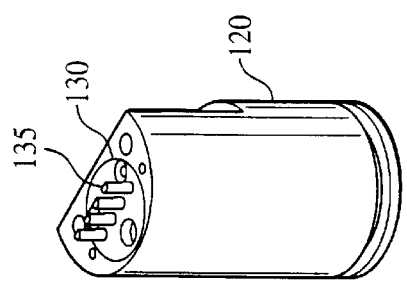

The configurations of the leadscrew riders 145 are designed so that the leadscrew riders 145 do not impede the Z positioning of other leadscrew riders 145. In FIG. 16D, the fine leadscrews 135 are inserted into leadscrew bearings in an inner cylinder 125 such that the stops of the leadscrew riders 145 fit into corresponding leadscrew rider channels in the inner cylinder, recall leadscrew bearings 620 and leadscrew rider channels 630 shown in FIGS. 6A–6D and leadscrew rider stops 1007 shown in FIGS. 10A–10D. In FIG. 16E, the inner cylinder 125 including the fine leadscrews 135, leadscrew collars 140, and leadscrew riders 145, is inserted into a passage of an outer cylinder 120. Before inserting the inner cylinder 125 into the outer cylinder 120, a sealing member is preferably positioned in the passage of the outer cylinder 120, recall passage 520 shown in FIGS. 5A–5D. An inner cylinder cap 130 is placed over the inner cylinder 125 sealing the passage of the outer cylinder 120. The upper portions of the fine leadscrews 135 protrude through leadscrew locator holes in the inner cylinder cap 130, recall leadscrew locator hole 710 shown in FIGS. 7A–7D. In FIG. 16F, the outer cylinder 120 is inserted through a passage in a lower plate 115, recall passage 415 shown in FIGS. 4A–4D. A ledge of the construction of the outer cylinder 120 contacts the lower plate 115 controlling the extension of the outer cylinder 120 through the lower plate 115. In FIG. 16G, an upper plate 110 is placed upon the lower plate 115 such that the outer cylinder passes through a passage in the upper plate, aligning the upper plate 110 with the lower plate 115, recall passage 315 shown in FIGS. 3A–3D. In FIG. 16H, a protective cap 105 is placed over the CCMD. Set screw holes in the protective cap 105 align with the corresponding set screw indentation in the lower plate 115 to secure the protective cap 105 in place, recall set screw holes 205 shown in FIGS. 2A–2D, and set screw indentation 402 shown in FIGS. 4A–4D. As noted above, the protective cap 105 is preferably removed when the electrodes are being positioned and during recording.

FIGS. 17A–17H show the same assembly process illustrated in FIGS. 16A–16H from a different perspective.

Figure 18:
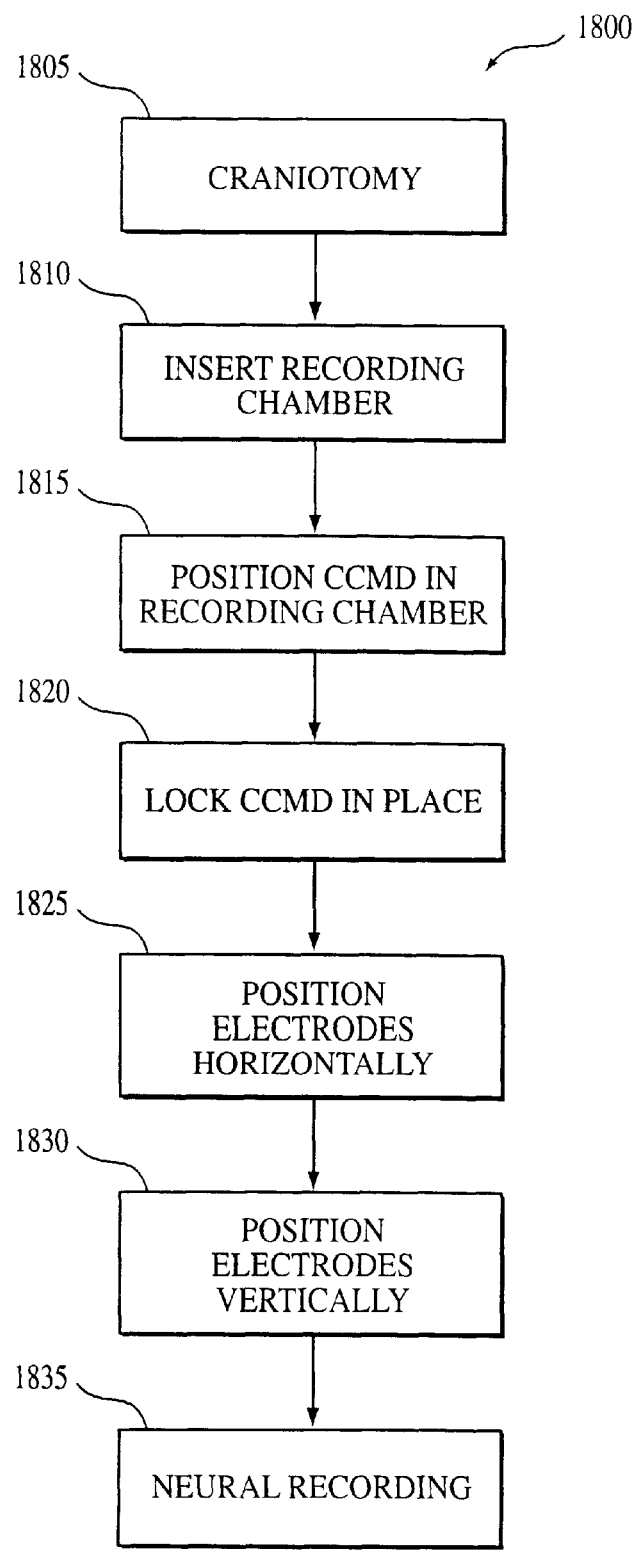
FIG. 18 is a flowchart of a process of neural recording using a CCMD recording to the present disclosure.

FIG. 18 shows a process 1800 of neural recording using a CCMD recording to the present disclosure. Initially, a craniotomy is performed upon a subject to expose a target site for a neural recording using conventional surgical techniques, step 1805. A conventional recording chamber 1810 is inserted into the cavity created by the craniotomy, step 1810. A CCMD configured as described above, is positioned in the recording chamber, step 1815. The O-ring seals of the CCMD, between the outer cylinder and recording chamber and between the outer and inner cylinders, provide a seal between the recording chamber and the CCMD such that the target site is no longer externally exposed. The CCMD is locked in place using set screws and hold-down screws as appropriate, step 1820. Electrodes previously positioned in leadscrew riders within the CCMD are horizontally positioned by independent rotation of the lower plate and inner cylinder of the CCMD, step 1825. The rotation can be automated or manual. As described above, the non-concentric nature of the inner cylinder and lower plate provides complete access for the electrodes to an available XY area defined by the inner diameter of the recording chamber subject to an unavailable ring area defined by the physical configuration of the components of the CCMD, as described below. The electrodes are positioned vertically by rotation of the fine leadscrews and hence Z translation of the corresponding leadscrew riders within the CCMD, step 1830. The Z position of the electrodes determines the depth of insertion into the neural tissue for a neural recording. Having positioned the electrodes, neural recording commences, step 1835.

As noted above, the seal provided by the CCMD and the recording chamber as well as the positioning provided by the dual non-concentric cylinder configuration and use of fine leadscrews allows for repeated acute neural recording and chronic neural recording. These neural recording sessions can be interleaved and/or repeated as appropriate. For example, after positioning the CCMD, the electrodes can be positioned for acute neural recording to test a portion of an exposed target site and then repositioned as necessary to find an "ideal" location for chronic neural recording. After finding such an ideal location, chronic neural recording can proceed without repeated surgical intervention due to the seals provided by the CCMD and recording chamber and without repositioning the CCMD. After the chronic neural recording session has completed, the electrodes can be repositioned to another location for chronic neural recording, optionally using another series of acute neural recording sessions to locate such a location.

Figure 19:
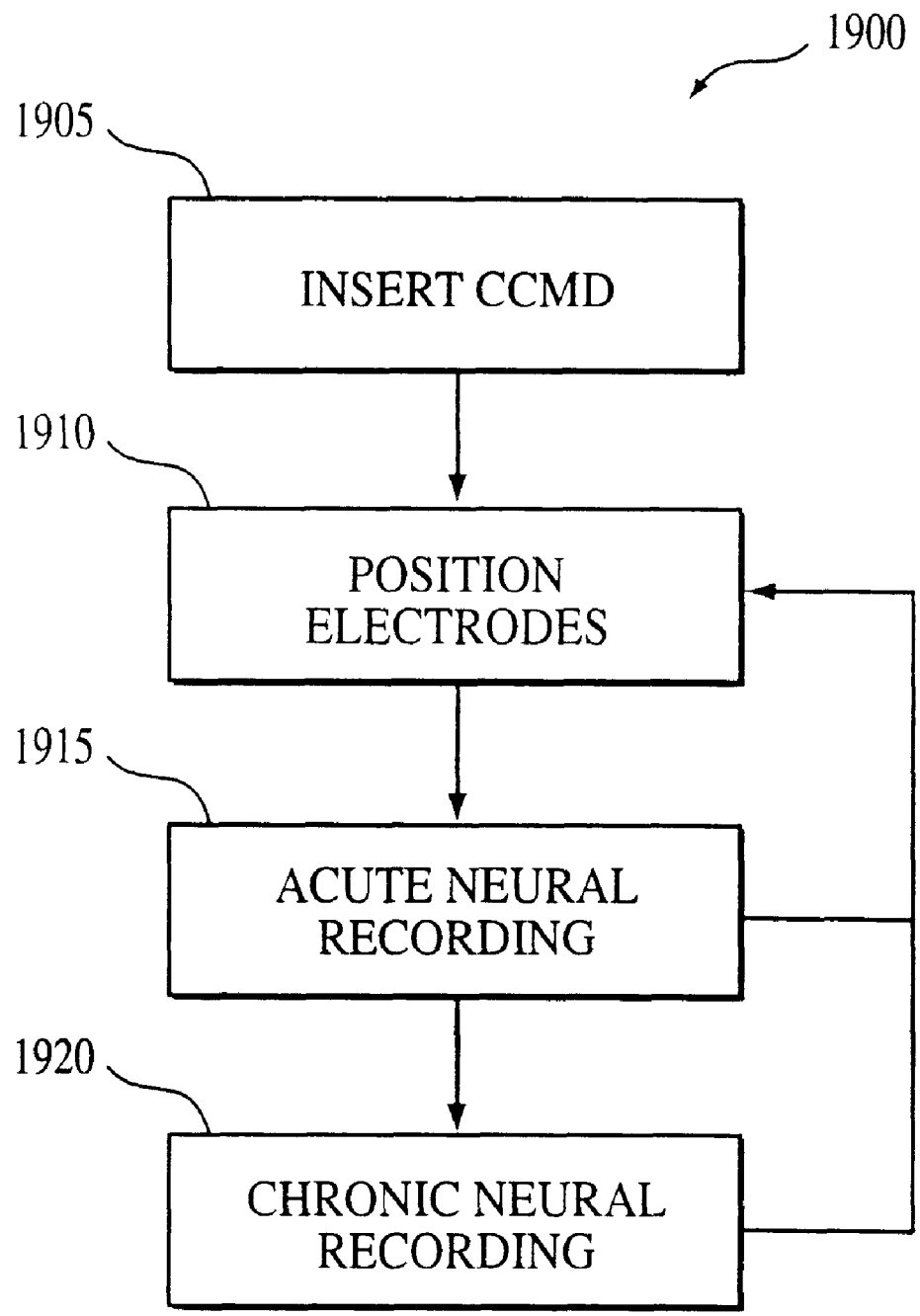
FIG. 19 is a flowchart of a process of using acute neural recording sessions in conjunction with chronic neural recording sessions.

FIG. 19 illustrates a process 1900 of using acute neural recording sessions in conjunction with chronic neural recording sessions. The CCMD is inserted into a previously prepared recording chamber above a target site for neural recording, step 1905. As described above, the electrodes are positioned horizontally and vertically using rotation of cylinders and fine leadscrews to place the electrodes at a target location in the neural tissue for neural recording, step 1910. An acute neural recording session proceeds to determine the neural characteristics of the current location, step 1915. Alternatively, the acute neural recording can be performed using a conventional microdrive. If the current position of electrodes does not produce desirable results, the electrodes can be repositioned for another acute neural recording session, step 1910. If the results of the acute neural recording session indicate that the current location is desirable, a chronic neural recording session proceeds, step 1920. Between neural recording sessions, the protective cap is preferably placed upon the CCMD to protect the CCMD. When the chronic neural recording session has completed, the electrodes can once again be repositioned to inspect other sites for potential usefulness as chronic neural recording sites, step 1910, or the CCMD can be removed concluding the neural recording process for this target site.

Figure 20A:
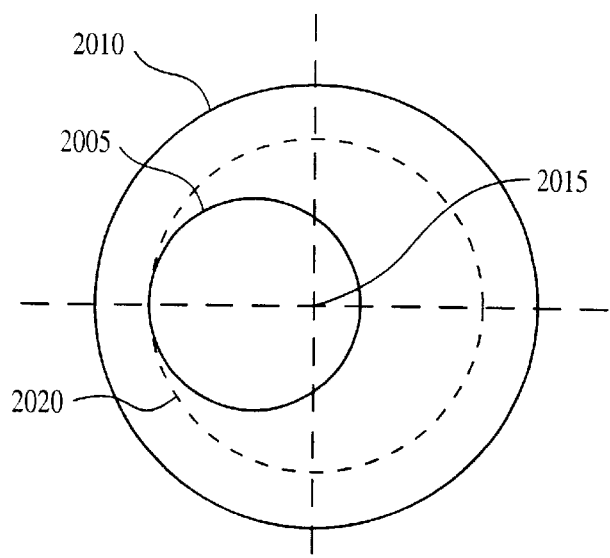
FIGS. 20A–20C illustrate the available XY positioning area provided by a CCMD according to the present disclosure.
Figure 20B:
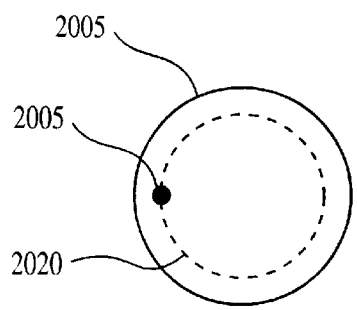
Figure 20C:
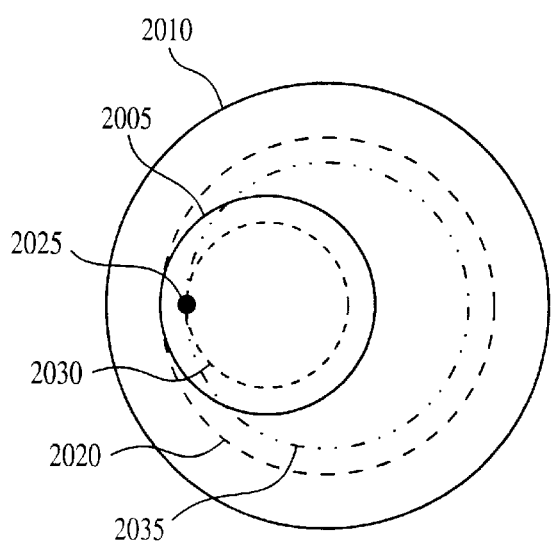

FIGS. 20A–20C illustrate the available XY positioning area provided by a CCMD according to the present disclosure. In FIG. 20A, an inner cylinder 2005 is positioned within an area defined by a lower plate 2010, recall lower plate 115 and inner cylinder 125 in FIGS. 1A–1D. The inner cylinder 2005 and the lower plate 2010 are non-concentric. In addition, the inner cylinder 2005 is positioned such that at least a portion of the inner cylinder overlaps the center 2015 of the lower panel 2010, where the longitudinal axis of the CCMD passes through the center 2015 and is perpendicular to the upper surface of the lower plate 2010. By rotating the lower plate 2010, the inner cylinder revolves through the area defined by the lower panel defining a covered area 2020. Depending upon the configuration of the inner cylinder 2005 and the lower plate 2010, the distance between the area 2020 and the perimeter of the lower plate 2010 can vary. However, the position of the electrodes does not exceed the area 2020.

FIG. 20B shows the area defined by the inner cylinder 2005 and the electrodes 2025 positioned in the inner cylinder 2005. By rotating the inner cylinder 2005, the electrodes 2025 revolve through the area defined by the inner cylinder 2005. This revolution defines a circle 2030 of potential positions for the electrodes within the area defined by the internal cylinder 2005. Similar to FIG. 20A, a space remains between the circle of revolution 2030 of the electrodes 2030 and the edge of the area defined by the inner cylinder 2005. The electrodes generally do not position outside the circle 2030. Accordingly, as described below, this space between the inner cylinder 2005 and the circle of revolution 2030 defines an area in which the electrodes are not positioned.

FIG. 20C illustrates the combined effect of rotating the lower plate 2010 and rotating the inner cylinder 2005 upon the position of the electrodes 2025. Due to the spacing between the inner cylinder 2005 and the edge of the lower plate 2010, a space remains unavailable for positioning between the area 2020 defined by revolution of the inner cylinder 2005 and the edge of the lower plate 2010. In addition, due to the position of the electrodes 2025 in the inner cylinder 2005 the revolution of the electrodes 2025 in the inner cylinder 2005 defines a circle of revolution 2030. By rotating the lower plate 2010, the inner cylinder 2005 revolves through the area defined by the lower plate 2010. Thus, the position of the electrodes 2025 can sweep through an area 2035 defined by the radially outwardmost position of the electrodes 2025 relative to the center of the lower plate 2010. This area 2035 defines the available XY positioning area. Thus, the available XY positioning area 2035 is limited by the spacing between the position of the electrodes 2025 in the inner cylinder 2005 and the position of the inner cylinder 2005 relative to the lower plate 2010. In alternative configurations and implementations, the amount of space lost in this way can be varied through design of the components of the CCMD.

Numerous exemplary implementations and applications have been described. However, additional variations are possible. For example, in the processes described above, non-order dependent steps can be performed in different sequences. Accordingly, the present disclosure is limited only by the scope of the following claims.

What is claimed is:

1. A device for neural recording from a target site of neural tissue exposed by an opening in a skull of a subject, comprising:

an outer cylinder, having a longitudinal axis, positioned within the opening and rotatable within the opening;

an inner cylinder positioned within the outer cylinder, such that the longitudinal axis of the outer cylinder is within a circumference of the inner cylinder and the inner cylinder rotates within the rotatable outer cylinder;

at least one fine leadscrew, positioned longitudinally in the inner cylinder;

at least one probe for neural recording, where at least one of said probes is coupled to a corresponding one of said fine leadscrews, where said probes are positioned horizontally by rotating the outer cylinder and separately rotating the inner cylinder, and where said probes are positioned vertically by rotating said fine leadscrews.

2. The device of claim 1, where at least one of said probes is an electrode.

3. The device of claim 1, where at least one of said probes is a non-electrical probe.

4. The device of claim 1, where at least one of said probes is a microwire electrode.

5. The device of claim 1, where at least one of said probes is a microwire bundle.

6. The device of claim 1, further comprising:

a recording chamber, where the recording chamber is inserted into the opening in the skull and the outer cylinder is positioned longitudinally within the recording chamber; and at least one sealing member interposed between the outer cylinder and the recording chamber, such that the target site is not externally exposed by virtue of said sealing members and the device can be used for chronic neural recording.

7. The device of claim 1, further comprising at least one sealing member coupled to the outer cylinder and the recording chamber, such that the target site is not externally exposed by virtue of said sealing members, and the device can be used for chronic neural recording.

8. The device of claim 1, wherein each probe is coupled to a corresponding fine leadscrew with a leadscrew rider, where the leadscrew rider translates longitudinally along the fine leadscrew as the fine leadscrew is turned and is restricted in motion by a corresponding leadscrew rider channel in the inner cylinder.

9. The device of claim 1, further comprising a protective cap, where the protective cap is coupled to the outer cylinder.

10. A device for neural recording from a target site of neural tissue exposed by an opening in a skull of a subject, where the opening extends vertically from a surface of the skull towards the target site, comprising:

a recording chamber, where the recording chamber is inserted into the opening in the skull;

an upper plate;

a lower plate coupled to the upper plate and to the recording chamber;

an outer cylinder, having a longitudinal axis, where the outer cylinder passes through and is coupled to the upper plate and the lower plate such that the outer cylinder is positioned longitudinally within the recording chamber;

at least one sealing member interposed between the outer cylinder and the recording chamber, such that the target site is not externally exposed by virtue of said sealing members;

an inner cylinder positioned within the outer cylinder, such that the longitudinal axis of the outer cylinder is within a circumference of the inner cylinder and the inner cylinder rotates within the outer cylinder, where the inner cylinder includes at least one leadscrew rider channel;

a coarse leadscrew for vertically positioning the outer cylinder, where the coarse leadscrew passes through the upper plate and the lower plate and into the outer cylinder;

at least one fine leadscrew, positioned longitudinally in the inner cylinder;

an inner cylinder cap coupled to the inner cylinder, for holding said fine leadscrews in place horizontally;

at least one leadscrew collar coupled to a corresponding fine leadscrew, for holding the fine leadscrew in place against the inner cylinder cap;

at least one leadscrew rider, where each leadscrew rider translates longitudinally along a corresponding fine leadscrew as the fine leadscrew is turned and is restricted in motion by a corresponding leadscrew rider channel in the inner cylinder;

at least one electrode for neural recording, where at least one of said electrodes is coupled to a corresponding one of said fine leadscrews, where said electrodes are positioned horizontally by rotating the outer cylinder and separately rotating the inner cylinder, and where said electrodes are positioned vertically by rotating said fine leadscrews.

11. A method of neural recording, comprising:

surgically creating an opening in a skull of a subject, where the opening exposes a target site of neural tissue;

inserting a recording chamber into the opening;

inserting a microdrive device into the recording chamber, where the microdrive device includes:
  an outer cylinder,
  an inner cylinder which is not concentric with the outer cylinder,
  a coarse leadscrew coupled to the outer cylinder;
  at least one fine leadscrew positioned within the inner cylinder,
  at least one electrode, where at least one electrode is coupled to a find leadscrew,
  a sealing member, and
  where inserting the microdrive device into the recording chamber forms a seal with the microdrive device, sealing member, and recording chamber such that the target site is not externally exposed;

horizontally positioning said electrodes at a first horizontal position by rotating the outer cylinder and separately rotating the inner cylinder;

vertically positioning said electrodes at a first vertical position by rotating the coarse leadscrew and separately rotating said fine leadscrews, such that the electrodes penetrate the target site and enter the neural tissue;

recording electrical activity in the neural tissue at the first horizontal position and the first vertical position using the electrodes.

12. The method of claim 11, further comprising:

vertically positioning said electrodes at a second vertical position by rotating said fine leadscrews, such that the electrodes penetrate the target site and enter the neural tissue, without removing the microdrive device from the recording chamber such that the seal is maintained;

recording electrical activity in the neural tissue at the second vertical position using the electrodes.

13. The method of claim 11, further comprising:

horizontally positioning said electrodes at a second horizontal position by rotating the outer cylinder and separately rotating the inner cylinder, without removing the microdrive device from the recording chamber such that the seal is maintained;

vertically positioning said electrodes at a second vertical position by rotating said fine leadscrews, such that the electrodes penetrate the target site and enter the neural tissue, without removing the microdrive device from the recording chamber such that the seal is maintained;

recording electrical activity in the neural tissue at the second horizontal position and the second vertical position using the electrodes.

14. A method of neural recording, comprising:

exposing a target site of neural tissue;

positioning one or more electrodes at a first target position in the neural tissue using a microdrive device;

recording neural activity at the first target position using said electrodes;

repositioning said electrodes at a second target position in the neural tissue using the microdrive device, without removing the microdrive device from the target site; and recording neural activity at the second target position using said electrodes.

15. The method of claim 14, where a recording chamber is coupled to the target site.

16. The method of claim 15, where the microdrive device is coupled to the recording chamber.

17. The method of claim 14, further comprising sealing the target site with the microdrive device, such that the neural tissue of the target site is not externally exposed.

18. The method of claim 17, where repositioning said electrodes does not break the seal and externally expose the target site.

19. The method of claim 14, where said recording neural activity at the first target position includes acute neural recording, and said recording neural activity at the second target position includes acute neural recording and chronic neural recording.

20. The method of claim 14, where said recording neural activity at the first target position includes chronic neural recording.

21. The method of claim 14, where said recording neural activity at the second target position includes chronic neural recording.

22. A method of neural recording using the device of claim 1, comprising:

exposing a target site of neural tissue;

positioning one or more electrodes at a first target position in the neural tissue;

recording neural activity at the first target position using said electrodes;

repositioning said electrodes at a second target position in the neural tissue; and recording neural activity at the second target position using said electrodes.

23. The method of claim 22, where said recording neural activity at the first target position is performed using the device of claim 1.

24. The method of claim 23, where said recording neural activity at the first target position includes chronic neural recording.

25. The method of claim 22, where said recording neural activity at the second target position is performed using the device of claim 1.

26. The method of claim 25, where said recording neural activity at the second target position includes chronic neural recording.

* * * * *